(12) United States Patent  
Moon et al.

(10) Patent No.: US 7,171,975 B2  
(45) Date of Patent: Feb. 6, 2007

(54) FABRICATION OF ULTRA-SHALLOW CHANNELS FOR MICROFLUIDIC DEVICES AND SYSTEMS

(75) Inventors: James E. Moon, Fairport, NY (US); Lincoln C. Young, Ithaca, NY (US)

(73) Assignee: Kionix, Inc., Ithaca, NY (US)

( * ) Notice: Subject to any disclaimer, the term of this patent is extended or adjusted under 35 U.S.C. 154(b) by 583 days.

(21) Appl. No.: 10/366,087

(22) Filed: Feb. 12, 2003

(65) Prior Publication Data

US 2003/0178075 A1   Sep. 25, 2003

Related U.S. Application Data

(60) Provisional application No. 60/356,493, filed on Feb. 12, 2002.

(51) Int. Cl.
  *F15C 1/06* (2006.01)
  *H01L 21/461* (2006.01)
(52) U.S. Cl. .................. 137/15.01; 137/833; 438/693; 438/704
(58) Field of Classification Search ................ 137/833, 137/15.01; 438/50, 52, 53, 693, 704
See application file for complete search history.

(56) References Cited

U.S. PATENT DOCUMENTS

| | | | | |
|---|---|---|---|---|
| 5,618,760 A | * | 4/1997 | Soh et al. | 438/703 |
| 6,729,352 B2 | * | 5/2004 | O'Connor et al. | 137/827 |
| 6,790,698 B2 | * | 9/2004 | Miller et al. | 438/50 |
| 6,880,576 B2 | * | 9/2004 | Miller et al. | 137/806 |
| 6,899,137 B2 | * | 5/2005 | Unger et al. | 137/833 |

* cited by examiner

*Primary Examiner*—A. Michael Chambers
(74) *Attorney, Agent, or Firm*—Jones, Tullar & Cooper, P.C.

(57) ABSTRACT

A method for etching an ultra-shallow channel includes using an etch process that is selective for one material to etch a different material in order to achieve a very precise channel depth in the different material. Channels as shallow as 10 nm can be fabricated in silicon with precision of 5 nm or better using the method. Stepped channels can be fabricated where each segment is a different depth, with the segments being between 10 nm and 1000 nm in depth. The method is applied to create a fluidic channel which includes a channel substrate to which is bonded a lid substrate to confine fluids to the fluidic channels so fabricated.

81 Claims, 25 Drawing Sheets

FABRICATION OF ULTRA-SHALLOW CHANNELS FOR MICROFLUIDIC DEVICES AND SYSTEMS

CROSS-REFERENCE TO RELATED APPLICATIONS

This application claims priority under 35 U.S.C. §119(e) based on U.S. Provisional Application Ser. No. 60/356,493 filed Feb. 12, 2002 and entitled FABRICATION OF SHALLOW AND ULTRA-SHALLOW CHANNELS FOR MICROFLUIDIC DEVICES AND SYSTEMS, incorporated herein by reference in its entirety.

FIELD OF THE INVENTION

This invention relates generally to the field of design, development and manufacturing of miniaturized chemical and biochemical analysis devices and systems using microelectromechanical systems (MEMS) technology, and more particularly to process sequences for fabricating MEMS and microfluidic devices and systems having fluid transport systems with any or all of the following attributes: (1) ultra-shallow depths; (2) well-controlled variations in channel depth; and (3) structures in the channels of sub-micrometer size.

BACKGROUND OF THE INVENTION

The creation of channels in a substrate at a microminiaturized scale has many potential applications. When suitably enclosed so as to confine the motion of a fluid to the channel, these structures may be used to provide a well-defined flow path for liquids or gases. Microchannels serve a wide variety of purposes, ranging from mere routing of fluid flow from a source to a destination or partitioning of a source volume into multiple streams; to mixing of two or more fluids for purposes of dilution, multi-phase extraction, or reaction; to chemico-physical interaction of the channeled fluid with physical structures created in the channel, e.g., for chromatographic separation; to analysis of fluid components by means of optical probing and other detection techniques.

Academic and commercial efforts to develop and manufacture fluidic channel devices and systems have utilized a variety of materials. The choice of materials has been dictated by performance requirements of the finished devices, by available processing equipment, and by individually established experience and familiarity with certain materials. A large body of published research details work on silicon, quartz, glass and plastic substrates.

Much early work was done with glass substrates or slides, generally for reasons of familiarity and compatibility with extant detection systems, or of ability to electrically insulate voltages ranging up to 10 kV in electrokinetically-driven separations.

Quartz substrates have also been used for fabrication of microchannel-based devices and systems, despite difficulties in processing due to the material's hardness and relative inertness.

Due to economically attractive materials costs, a variety of plastics have been considered and evaluated as substrate materials for microchannels. Although incompatibility with fluidic constituents can limit choice of specific materials due to possible contamination of transported fluids, the relatively inexpensive cost of plastics vis-a-vis glass or silicon substrates has driven continued work for certain applications.

Silicon has been regarded as a potentially valuable substrate for a wide variety of microelectromechanical applications for several decades. The relatively recent growth of interest in silicon as a substrate for microfluidic devices and systems is, in part, attributable to the emergence of process equipment that is suitable for fabricating structures with better-defined architectures and high aspect ratios.

Shallow channels may be formed from any of these materials. Shallow channels typically may be fabricated having dimensions from 1 to 100 µm in width, 1 to 100 µm in depth, and 10 µm to 10 mm in length. These dimensions correspond to a cross-sectional area of 1 to $10^4$ µm$^2$ and total contained fluid quantities of $10^1$ to $10^8$ µm$^3$, or 10 fL to 100 nL.

These dimensions offer the advantages of reduced fluid volume over macro systems. Very small quantities of fluids are needed to fill microchannels and, conversely, very small quantities of effluent fluid are produced. This constitutes a principal attraction of these structures.

Shallow channels also offer performance advantages: undesired dead volume originating from separate component interconnection can be significantly reduced or eliminated; operation time can be greatly lessened due to shortened fluid flow path lengths; more effective separations can be done due to increased surface-to-volume ratios; and greatly reduced quantities of solvents and reagents are required (with concomitant reduction of effluent volumes), as discussed previously.

Fabrication methods and equipment developed for the creation of standard semiconductor industry products like microprocessors, memory, and logic, and later used for the manufacturing of microelectromechanical systems (MEMS), are particularly well-suited for use in the creation of microfluidic channels in silicon. The art of creating intricate, multi-layer patterns in silicon and compatible materials through deposition, lithographic, and etching processes is extremely well developed and reproducible in those industries.

Dry etching of silicon, whether primarily physical in nature (ion-milling) or primarily chemical (plasma etching), is a highly evolved part of the overall MEMS fabrication process. Reactive-ion etching (RIE) is a method of etching that is a combination of physical and chemical mechanisms, and is the most commonly practiced embodiment of dry etching. RIE, through judicious selection and optimization of reactant gases, pressure, temperature, and power sources, can attain both a high degree of anisotropy as well as good selectivity (differentiation among unlike materials). A particular class of silicon etch processes has been considered specifically for high-aspect-ratio etching of silicon in MEMS applications.

Confinement of fluids to channels is an indispensable requirement for controlled operation of microfluidic devices and systems. Although three of the required four sides in a channel of rectangular cross-section may be formed as a natural consequence of the etching processes, the remaining side must be provided through additional process steps. There are a variety of methods by which a lid substrate may be attached to a channel substrate, including anodic bonding, fusion bonding, frit bonding, and attachment through the use of "glue" layers, generally organic in nature. Anodic bonding, when suitable for a given device and application, provides a strong, hermetic bond between a silicon substrate and a glass lid substrate.

Simple microfluidic systems may be enhanced by defining additional functionality in the fluidic device. The functionality defined may include electrospray ionization (ESI), liquid chromatography (LC), and integrated LC/ESI devices and systems. The additional functionality may be as simple as electrical contacts for purposes of effecting electrokinetic flow and separation in the channels. On the other hand, the incremental functionality may take the form of additional microstructures, such as nozzles for purposes of electrospray to transport fluids off-chip. Creation of the desired functionality can be commonly achieved by integration of appropriate additional patterns in design and layout as well as additional process operations. This offers a significant advantage over a system built by macroscopic assembly of individual components.

Other researchers have similarly considered microfluidic systems in which the basic functionality of microfluidic channels was enhanced through the creation of intra-channel structures.

Although device design for microfluidic applications entails consideration of often-challenging constraints that go beyond the basic creation of the microfluidic channels themselves, the fabrication of channels with dimensions of a micron or more as discussed above is generally straightforward.

Many applications have been identified and more are anticipated for channels that have been etched into a substrate such as silicon, glass, quartz, or fused silica with depth of channels typically ranging from 10 to 100 µm in depth. Such channels can be fabricated using known techniques. New applications are emerging, however, for channels that are $\frac{1}{10}$–$\frac{1}{1000}$ of those depths, i.e., depths ranging from approximately 10 to 1000 nm ("ultra-shallow channels"). Applications for ultra-shallow channels often require more precise tolerances than standard devices, thus increasing the fabrication challenge.

The typical etch processes described above are not capable of producing devices to such specification. RIE, for example, etches at rates that make sub-micron control difficult in any dimension. Also, whereas lateral dimensions are more easily varied (at least for critical dimensions greater than 1 µm) through layout in CAD, vertical differentiation of features (e.g., controllably varied channel depths) can be very difficult to achieve in currently-practiced processing schemes, and cannot be controlled at all reliably with sub-micron precision.

Fabrication of ultra-shallow channels is difficult to achieve with sufficient control for reproducibility in manufacturing. Standard etch processes and equipment are generally designed to maximize etch rate while maintaining at least a minimal level of other performance parameters like selectivity to masking materials. In the case of ultra-shallow channels, however, low etch rates are needed so as to afford an acceptable degree of precision. That is, in the absence of a detectable and definitive endpoint, etch depth is determined by etch time, given an established etch rate. For example, with a typical RIE etch rate of several micrometers per minute, a 50 nm channel would nominally require an etch time of only 1–2 seconds. Since there are transient plasma conditions after ignition that last several seconds during which etch rates and uniformities are not characteristic of the stabilized etch process, reproducibility of an etch of a few seconds duration is unachievable, and etch durations of less than two seconds produce inherently unreliable results.

There is a need for devices having ultra-shallow channels. Ultra-shallow channel devices meet some of the following requirements: minimizing fluid volume; maximizing interaction with channel surfaces (high surface-to-volume ratio); controlling the flow of a transported fluid in the laminar or molecular flow regime; acting as a filter for particles of greater dimension than the channel depth; and increasing the signal-to-noise (S/N) ratio for optical probing techniques by limiting the required depth of field in optical detection systems and other factors. Current state of the art processes cannot produce devices incorporating ultra-shallow channels reliably or repeatably.

SUMMARY OF THE INVENTION

The present invention addresses the aforementioned drawbacks by providing a method for producing devices having ultra-shallow channels.

We herein disclose a method whereby ultra-shallow channels may be fabricated with required precision and reproducibility. Any given etch process, to be effective, preferentially etches one material at a relatively fast rate, and is less effective in etching a second material that is simultaneously presented for etching. In such an example, the etch process is said to be selective for the first material, and selective to the second. The degree of selectivity is expressed as the ratio of the etch rate of the intended material to the etch rate of the unintended material. Standard fabrication processes utilize etch methods selective for the substrate sought to be etched in order to increase the efficiency of the process, controlling the etch of the substrate with a relatively non-reactive masking material patterned on the wafer. We achieve the required control necessary to create ultra-shallow channels in the substrate by reversing this process altogether, using an etch that is selective for the mask and to the substrate. This permits much more fine control of the rate of etch of the substrate. The disclosed method has been shown to have a precision of 5 nm or better, and can be used to reproducibly fabricate channels as shallow as 10 nm or less.

This method is compatible with either resist-masked etching or etching without resist mask. In one embodiment of the invention, silicon oxide is patterned as a mask over a silicon substrate, and an etch method selective for silicon oxide is employed on the patterned silicon wafer. The silicon oxide will be consumed at a much faster rate than the silicon according to well-established selectivity ratios. In this manner, by regulating the thickness of the silicon oxide mask, the exposed silicon can be etched with great precision.

In another alternative embodiment, a process designed to etch silicon preferentially to silicon oxide may be used to etch ultra-shallow channels in silicon oxide. Masking in this case would be done using lithographically patterned photoresist, for example.

In yet another embodiment, the method is used to etch structures other than fluidic channels to ultra-shallow depths. Any pattern that can be defined by lithographic means can be transferred to the desired depth using the disclosed method. For example, damascene (inlaid) structures may be fabricated using the disclosed method. Potential applications for this embodiment include, but are not limited to, the following: (1) Creation of metal or metal-like wires for conduction of electrical and/or thermal signals on the device, while preserving a planar top surface of the substrate so as not to impede bonding to another substrate. (2) Creation of an island of heterogeneously doped silicon/polysilicon (as compared to surrounding substrate material), with the additional refinement possible of electrically isolating the so-created island from the surrounding substrate by means of a thermally grown or deposited insulating material like silicon oxide between the substrate and the island. The island could serve as an etch stop for a dopantdependent etch, for example. (3) Creation of structures that can subsequently, through additional process steps, be released from the surrounding substrate, thereby having suspended structures that are free to move except at designed anchor points. (4) Creation of features that can subsequently, through an embossing process, be transferred in relief to a removable material like a thermally-deformable plastic.

Fluidic channels or other features that have been fabricated by the disclosed method can be passivated if desired by subsequent thermal growth of silicon oxide or by conformal deposition of silicon oxide or silicon nitride. The ultra-shallow fluidic channels or structures so formed—whether passivated or unpassivated—are compatible with a variety of bonding methods for purposes of providing a necessary containing surface for the channels.

A method is also disclosed whereby stepped fluidic channels may be fabricated. Stepped fluidic channels are channels having two or more different discrete depths. Each channel segment corresponds to a separate masking and etching sequence. Any or all of the channel segments may be etched to ultra-shallow depths using the method previously disclosed. Any or all of the stepped channel segments may be ultra-shallow in depth. We also disclose means by which relatively deep channel segments may be produced contiguous to ultra-shallow segments. By thus combining normal etching with ultra-shallow etching, extreme variations in channel depth can be produced—e.g., 100 μm in combination with 10 nm segments, a $10^4$ depth ratio. Such a structure could function as a kind of pressure relief, or overpressure, valve.

As in the case of channels and/or structures of ultra-shallow depth, the surfaces of stepped channels may be passivated by thermal growth of silicon oxide or by the deposition of a passivating film like silicon oxide or silicon nitride. The ultra-shallow fluidic channels or structures so formed are compatible with a variety of bonding methods for purposes of providing a necessary containing surface for the channels.

In a third aspect of the present invention, structures such as posts, weirs, flow steering/mixing barriers, etc., can be patterned within defined channel(s), and are formed at the same time as the channel walls when the channel is etched. Formation of such structures is entirely compatible with the former two aspects of the present invention. The structures may be formed in ultra-shallow channels, as well as any or all levels of a multi-stepped channel.

The tops of the structures can be made to be co-planar with the field region (the preferred embodiment) so as to facilitate and ensure sealing to a bonded surface and to prevent formation of a fluidic "sneak path". Alternatively, the structures can be fabricated such that their tops can be at the level of the shallower channel in a stepped channel. This is accomplished by appropriate segregation of the structure patterns between masks corresponding to the separate channel segments.

As in the case of channels and/or structures of ultra-shallow depth(s), the surfaces of structures formed in the channels may be passivated by thermal growth of silicon oxide or by the deposition of a passivating film like silicon oxide or silicon nitride. The ultra-shallow fluidic channels or structures so formed are compatible with a variety of bonding methods for purposes of providing a necessary containing surface for the channels.

A microfluidic channel system is also disclosed, comprising a channel substrate (silicon, in one embodiment), to which is bonded a second substrate so as to provide a containing surface for the fluid. The second substrate can be passive, in the sense that it merely bounds the fluidic channel(s) in the channel substrate. Ingress and egress to/from the fluidic channel would functionally be a part of the channel substrate in this case. The second substrate may also provide access for optical probing techniques if suitably transmissive to the wavelengths of the probing electromagnetic light source. Alternatively, the second substrate can be active, in the sense that it provides access to the fluidic channels in the channel substrate in addition to its primary function of bounding the fluid channel(s).

In another embodiment, the fluidic channels can be continuous to the edge of the finished and diced device so as to provide means of fluidic ingress and/or egress to/from the fluidic channels.

Briefly stated, a method for etching an ultra-shallow channel includes using an etch process selective for one material on a different material that is selective to that same process in order to achieve a very precise channel depth in the different material. Channels as shallow as 10 nm can be fabricated in silicon with precision of 5 nm or better using the method. Stepped channels can be fabricated where each segment is a different depth, with the segments being between 10 nm and 1000 nm in depth. The method is applied to create a fluidic channel, which includes a channel substrate to which is bonded a lid substrate to confine fluids to the fluidic channels so fabricated.

According to an embodiment of the invention, a method for etching an ultra-shallow channel includes the steps of providing a substrate of a first material; forming a layer of a second material on at least part of said first material; selectively removing a portion of said second material such that said second material is completely removed in at least one area to expose at least one area of said first material and is at least partially persistent in areas adjacent to said at least one exposed area of said first material so as to provide direct etchant communication with said first material within said at least one exposed area and to prevent etchant communication with said first material in areas where said second material has not been completely removed, and such that said act of removing said portion of said second material does not significantly remove any of said first material; providing an etch process that is selective for said second material and selective to said first material, wherein said etch process preferentially etches said second material at a rate that is significantly greater than that at which said etch process would etch said first material; and applying said etch process to etch said first material to a desired depth of said ultra-shallow channel.

According to an embodiment of the invention, a method for etching an ultra-shallow channel includes the steps of providing a substrate of a first material; forming a masking layer of a second material on at least part of said first material; coating said masking layer with a photoresist layer; defining a pattern in said photoresist layer; transferring said pattern into said masking layer using a dry etching process selective for said second material at a first etch rate until said first material is exposed; and etching said exposed first material using said dry etching process at a rate less than said first etch rate until a desired depth of said ultra-shallow channel is achieved in said first material.

According to an embodiment of the invention, a method for etching an ultra-shallow channel includes the steps of providing a substrate of a first material; forming a masking layer of a known depth of a second material on at least part of said first material; determining a first etch rate of a dry etching process in said first material where said dry etching process is selective for said second material; determining a second etch rate of said dry etching process in said second material; coating said masking layer with a photoresist layer; defining a pattern in said photoresist layer; transferring said pattern into said masking layer using said dry etching process; and continuing etching said first material using said dry etching process until a desired depth of said channel is achieved in said first material, where a total time for etching said first and second materials is determined by dividing said desired depth in said first material by said first etch rate to obtain a first time, dividing said known depth of said masking layer by said second etch rate to obtain a second time, and adding said first and second times together to obtain said total time.

According to an embodiment of the invention, a method for etching an ultra-shallow channel includes the steps of providing a substrate of a first material; coating said first material with a photoresist layer; defining a pattern in said photoresist layer; transferring said pattern into said first material using a dry etching process selective for a material other than said first material until a desired depth of said channel is achieved in said first material.

According to an embodiment of the invention, a method for etching an ultra-shallow channel in a workpiece includes the steps of providing a substrate of a first material; forming a layer of a second material on at least part of said first material; coating said layer with a photoresist; defining a pattern in said photoresist; and transferring said pattern into said layer using a dry etching process selective for said first material until a desired depth of said channel is achieved in said second material.

According to an embodiment of the invention, a method for creating a structure that is attached to a substrate only at designated anchor points, thus permitting free movement of said structure except at said anchor points, includes the steps of providing a workpiece initially consisting of a substrate of a first material; forming a layer of a second material on at least part of said first material; coating said layer with a photoresist; defining a pattern for said anchor points in said photoresist; transferring said pattern into said layer using a dry etching process selective for said first material until a depth of said pattern in said second material extends to said substrate; depositing said first material in said pattern, thereby filling said pattern; smoothing said first material until a top side of said first material is coplanar with a top side of said second material; depositing said first material on said workpiece followed by patterning said first material; and etching, using a wet etch, to remove said second material, thereby leaving said patterned first material and said substrate connected only by non-patterned regions of said workpiece.

According to an embodiment of the invention, a method for etching a channel includes the steps of providing a substrate of a first material; forming a masking layer of a second material on at least part of said first material; coating said masking layer with a first photoresist layer; defining a first pattern for a first segment of said channel in said first photoresist layer; transferring said first pattern into said masking layer using a dry etching process selective for said second material at a first etch rate until said first material is exposed; etching, at a second etch rate, said exposed first material using said dry etching process until a desired depth of said first segment of said channel is achieved in said first material; removing said first photoresist layer from said masking layer; coating said masking layer and said first segment with a second photoresist layer; defining a second pattern for a second segment of said channel in second photoresist layer; transferring said second pattern into said masking layer using said dry etching process selective for said second material until said first material is exposed; etching said exposed first material using said dry etching process until a desired depth of said second segment of said channel is achieved in said first material, wherein said first and second segments have different depths; and removing said second photoresist layer from said masking layer and said first segment.

According to an embodiment of the invention, a method for etching a channel in a workpiece includes the steps of providing a substrate of a first material as an initial form of said workpiece; forming a masking layer of a second material on at least part of said first material; coating said workpiece with a first photoresist layer; defining a first pattern for a first segment of said channel in said first photoresist layer; transferring said first pattern into said masking layer using a dry etching process selective for said second material until said first material is exposed; removing said first photoresist layer from said workpiece; coating a second photoresist layer on said workpiece; defining a second pattern for a second segment of said channel on said second photoresist layer, wherein said second pattern includes said first pattern as a subset; dry etching, after the step of defining said second pattern, said first pattern into said first material for a first period of time; transferring said second pattern into said masking layer using dry etching; and dry etching simultaneously, using said dry etching process and after the step of transferring said second pattern, said first and second patterns for a second period of time, such that the planar dimensions of said first pattern and said second pattern are reproduced in said substrate.

According to an embodiment of the invention, a method for etching a channel in a workpiece includes the steps of providing a substrate of a first material as an initial form of said workpiece; forming a masking layer of a second material on said workpiece; coating a first photoresist layer on said masking layer; defining a first pattern for first and second segments of said channel on said first photoresist layer; transferring said first pattern into said masking layer to a depth of an interface between said first material and said second material using dry etching; removing said first photoresist layer from said workpiece; coating a second photoresist layer on said workpiece; defining a second pattern on said workpiece, wherein said second pattern corresponds to said first segment of said channel; dry etching, after the step of defining said second pattern, said second pattern into said first material for a first period of time; removing said second photoresist layer from said workpiece; dry etching simultaneously, using said dry etching process and after the step of dry etching said second pattern, said first and second segments for a second period of time, such that the planar dimensions of said first segment and said second segment are reproduced in said substrate.

According to an embodiment of the invention, a method for making a plurality of posts in an ultra-shallow channel in a workpiece includes the steps of providing a substrate of a first material; forming a layer of a second material on at least part of said first material; coating said layer with a photoresist; defining a pattern for said plurality of posts in said photoresist such that said plurality of posts are masked from etching; and transferring said pattern into said layer using a dry etching process selective for said first material until a desired depth of said channel is achieved in said second material.

According to an embodiment of the invention, a method for etching a channel includes the steps of providing a substrate of a first material; forming a masking layer of a second material on at least part of said first material; coating said masking layer with a first photoresist layer; defining a first pattern for a first segment and a second segment of said channel in said first photoresist layer; transferring said first pattern into said masking layer using a dry etching process selective for said second material at a first etch rate until said first material is exposed; etching, at a second etch rate, said exposed first material using said dry etching process until a desired depth of said first and second segments of said channel is achieved in said first material; removing said first photoresist layer from said masking layer; coating said masking layer and said first and second segments with a second photoresist layer; defining a second pattern for a third segment of said channel in said second photoresist layer; transferring said second pattern into said masking layer using said dry etching process selective for said second material until said first material is exposed; etching said exposed first material using said dry etching process until a desired depth of said third segment of said channel is achieved in said first material, wherein said third segment is a different depth from said desired depth of said first and second segments; and removing said second photoresist layer from said masking layer and said first and second segments.

According to an embodiment of the invention, an integrated fluidic channel system includes a fluidic channel silicon substrate having a first surface and a second surface; said channel substrate defining a channel origination portion, a channel terminus portion, and a shallow or ultra-shallow channel extending between said channel origination portion and said channel terminus portion on at least said first surface, wherein said shallow or ultra-shallow channel includes at least a first segment that is between 10–1000 nm in depth; at least one of said channel origination portion, said channel terminus portion, and said channel being formed at least in part by reactive-ion etching; and a lid substrate having a first surface and a second surface, wherein said second surface of said lid substrate is attached to said first surface of said channel substrate to enclose said channel origination portion, said channel terminus portion, and said channel.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

DETAILED DESCRIPTION OF THE PREFERRED EMBODIMENT

Figure 1A:
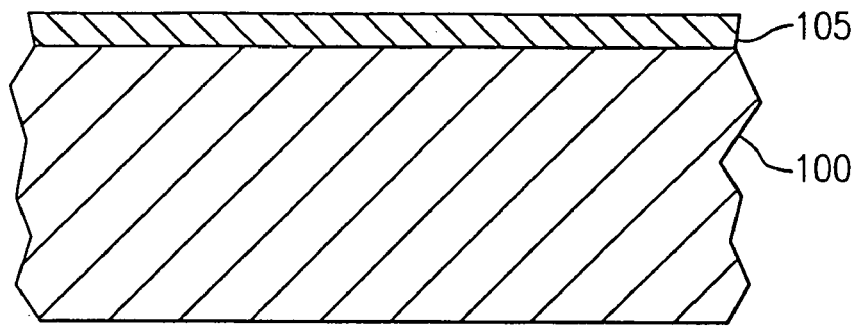
FIGS. 1A–1E show cross-sectional views of a process sequence that was followed to produce ultra-shallow channels according to an embodiment of the invention.

Reference will now be made in detail to the present exemplary embodiments of the invention, examples of which are illustrated in the accompanying drawings. Wherever possible, the same reference numbers will be used throughout the drawings to refer to the same or like parts.

The first principal aspect of the present invention addresses the formation of shallow and ultra-shallow fluid transport channels. "Shallow" as used herein means depths ranging from 1 µm to 10 µm. "Ultra-shallow" as used herein means depths below a micron ranging from 10 nm to 1000 nm (1 µm). "Standard" as used herein means depths ranging from 10 µm–100 µm, while "deep" means depths greater than 100 µm. One micron is chosen as the dividing line between shallow and ultra-shallow because conventional methods of fabrication do not work reliably below one micron.

Methods of fabrication are disclosed whereby sub-micrometer channel depths can be reproducibly created using standard semiconductor processing equipment. Channel depths as little as 10 nm are readily achieved using the disclosed methods.

A second principal aspect of the invention addresses the formation of stepped fluid transport channels—i.e., channels of purposefully varying depth along well-defined segments of the channel. Methods of fabrication are disclosed whereby channel depths ranging from 10 nm to hundreds of micrometers may be produced, with sharp, well-defined transition between contiguous channel segments.

In addition to the two principal aspects of the present invention, an alternative embodiment is disclosed wherein microstructures may be created within the ultra-shallow channels, whether they are of a single uniform depth or comprising more than one segment with discretely varying channel depths. The aforementioned microstructures may be used to effect a variety of purposes, including mixing and chromatographic separation.

Lastly, an alternative embodiment is disclosed wherein ultra-shallow channels with or without stepped depths and with or without microstructures in the channel(s) are combined with a second substrate so as to comprise a microfluidic channel system. The system provides for the preservation of the performance advantages obtained by the creation of the aforementioned channels, ensuring that designed volumes and cross-sectional profiles are retained in a practical, working microfluidic channel device and/or system, preventing dead volume creation and out-of-channel fluidic leakage.

Ultra-shallow Fluidic Channels—Methods of Fabrication

The formation of fluidic channels having depths less than 1–2 µm presents serious issues of process control and reproducibility. In commonly available reactive-ion etch (RIE) tools and processes, silicon etch rate ranges from 1–7 µm per minute. Indeed, tool and process designs would generally have the goal of maximizing silicon etch rate while preserving at least certain levels of selectivity to masking materials like silicon oxide or photoresist. Further, the nature of the Bosch etch is cyclical—i.e., a short series of 2–5 second steps (a "loop") is repeated for a user-chosen number of iterations, with each loop lasting about 12 seconds. This implies a best-case etch depth resolution of 0.2 µm, or 200 nm, with depths of 0.2, 0.4, 0.6 µm, . . . thus being available, but nothing between (or below 0.2 µm).

For precise control of cross-sectional dimensions, fluid volume and volumetric flow rates, it is generally necessary to have a fabrication process that would achieve etch-depth tolerances of less than ±5% and, for critical applications, less than ±1%. The etch depth resolution delivered by the standard etch process is therefore far too coarse to achieve targeted etch depths below 1–2 µm with precision.

Whereas established silicon etch tools and processes are developed to generally maximize silicon etch rate, they are simultaneously designed to minimize etch rates of common masking materials like silicon oxide or photoresist. Equivalently, the silicon etch rate is maximized while maintaining good selectivity to silicon oxide and photoresist, where selectivity is the ratio of silicon etch rate to mask etch rate. Common selectivity values range from 80:1–160:1 for oxide, 40:1–80:1 for photoresist. Conversely, equipment and etch processes that are designed to etch silicon oxide will have selectivity to silicon—that is, the etch rate of silicon oxide is high relative to that of silicon.

It will be appreciated that the present invention can be employed in the context of a semiconductor processing system for fabricating MEMS devices. Such a processing system might include, for example, a dry etcher configured to apply a dry etchant to at least one substrate (using a process such as reactive ion etching (RIE)) and a process controller coupled to the etcher. The process controller can be programmed to select a dry etchant having a predetermined etch rate relative to any particular substrate. While no one particular etchant is specifically preferred, it should be noted that the dry etchant can be a gas, such as $CHF_3$. The process controller also can direct the etcher to apply the selected etchant to at least a portion of the substrate for a predetermined period of etching time, so that the dry etcher etches in the substrate to a predetermined submicron etch depth for a predetermined period of etching time.

The etch depth, etching rate, and etching time, singly or in combination, may be adjusted to form desired submicron microstructures in the substrate. For example, the etch rate associated with advantageous operation of such a semiconductor processing system might have a lower boundary of approximately 1.5 nm per second. Further, the predetermined period might have a lower boundary of approximately three seconds.

The present invention discloses the use of an etch process that is designed and optimized for etching silicon oxide (in preference to etching silicon) to etch silicon, so as to dramatically lower the silicon etch rate for purposes of precision in etching extremely shallow channels. This method has been demonstrated to achieve targeted etch depths with precision (deviation from target) of less than 5 nm.

The mechanism for silicon to silicon oxide selectivity is understood in terms of a fluorine-to-carbon ratio (F/C). As the F/C ratio is lowered through choice of etch gases, the tendency to etch silicon is reduced. Also as hydrogen is introduced to the primary fluorine-supplying etch gas, F atoms are scavenged, thereby lowering the F/C ratio, and contributing to the deposition of non-volatile etch residue on the silicon surface, inhibiting silicon etching. In areas of silicon oxide, oxygen is supplied from the oxide to scavenge carbon, increasing the F/C ratio locally and helping to maintain oxide etch rate. With etching of silicon depressed (through the addition of hydrogen) and the etching oxide sustained by oxygen (supplied from the oxide itself), selectivity of silicon to oxide is achieved.

The hydrogen needed to increase silicon:oxide selectivity can be supplied explicitly in the form of hydrogen gas ($H_2$) in combination with a primary etchant gas like $CF_4$, typically in volumetric concentrations of hydrogen ranging up to 40%. Alternatively, the hydrogen may be supplied by the primary etchant gas itself, as in the case of $CHF_3$.

In the oxide etch process used to fabricate shallow-ultra-shallow channels as disclosed in the present invention, a single etch gas, $CHF_3$, was used at a flow rate of 30 sccm and a pressure of 5 mT. Helium backside cooling at 3000 mT was used to maintain stable etch temperatures at the wafer surface and to thereby help conserve masking photoresist. Dual electrodes were used to generate the etch plasma, with the source electrode at 650 W and 15° C., and the substrate electrode at 85 W and 30° C.

The foregoing etch process parameters resulted in an oxide etch rate of 200 nm/min and a silicon etch rate of 95 nm/min. By comparison, the silicon etch rate in the standard Bosch silicon etch process is roughly 2000 nm/min or more, over twenty times faster. With a silicon etch rate of roughly 1.5 nm/sec in the oxide etch process, etch depth precision of 5 nm or better corresponds to a little over 3 seconds of etch time, which is easily achieved under machine program control.

With respect to machine program control, the present invention can be executed, and perhaps even enhanced, using the advantages associated with computer control of manufacturing processes. In the context of the present invention, well-known computer readable media, such as random access memory (RAM), read only memory (ROM, EROM $E^2$ROM, etc.), CD/ROM, diskettes, optical media, magnetic media, electromagnetic media, wireline transmission media, wireless transmission media, fiber optic transmission media, or the like, can be used to store computer-executable instructions. The computer-executable instructions could then be executed by a computer associated with a MEMS fabrication system. Bearing in mind the processes described herein, the computer-executable instructions might include a method for making a microstructure, including selecting a dry etchant having a predetermined etch rate relative to a substrate, and directing an etcher to apply the selected etchant to at least a portion of the substrate for a predetermined period of etching time. The etchant is selected or formulated to etch in the substrate to a predetermined submicron etch depth during the predetermined period of etching time to thereby form submicron microstructures in the substrate.

Re-design of process tools can undoubtedly accomplish, at least to a degree, the significant reduction in silicon etch rate that is needed for precise control of ultra-shallow channel depths. This redesign would entail expenditure of significant non-recurring engineering funds.

Similarly, the existing etch process in extant etch equipment may be modified so as to effect, at least in part, a reduction in silicon etch rate, although this will likely come at the cost of increased maintenance due to excessively polymerizing etch chemistry, and/or reduction of process uniformity. The salient advantage of the present invention is its use of existing processes in existing etch equipment.

Figure 1B:
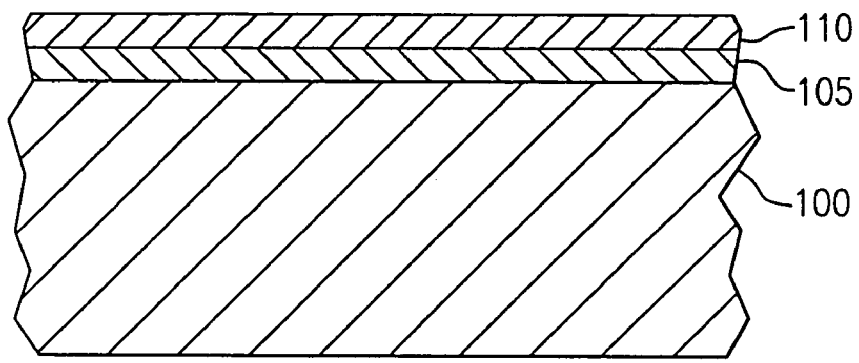
Figure 1C:
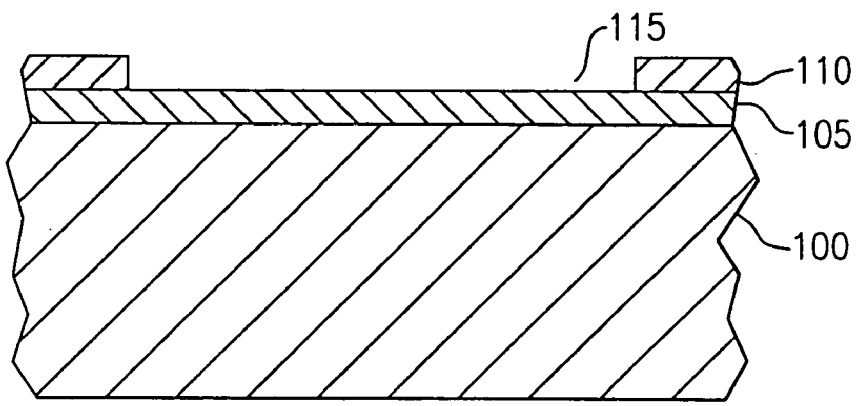

FIGS. 1A–1E show cross-sectional views of a process sequence that was followed to produce ultra-shallow channels. A silicon oxide film 105 is produced on a silicon substrate 100, either by thermal oxidation or by deposition using any of several standard methods (FIG. 1A). A film of photoresist 110 is then deposited on top of the oxide film 105 (FIG. 1B). Standard lithographic patterning by exposure and development then produces areas 115 in the photoresist film 110 that are open to the underlying oxide film 105 (FIG. 1C).

Figure 1D:
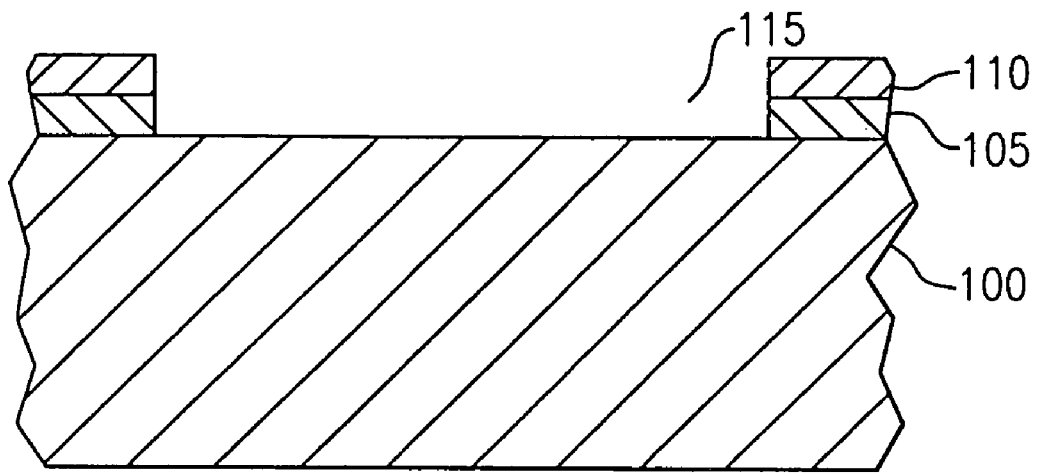
Figure 1E:
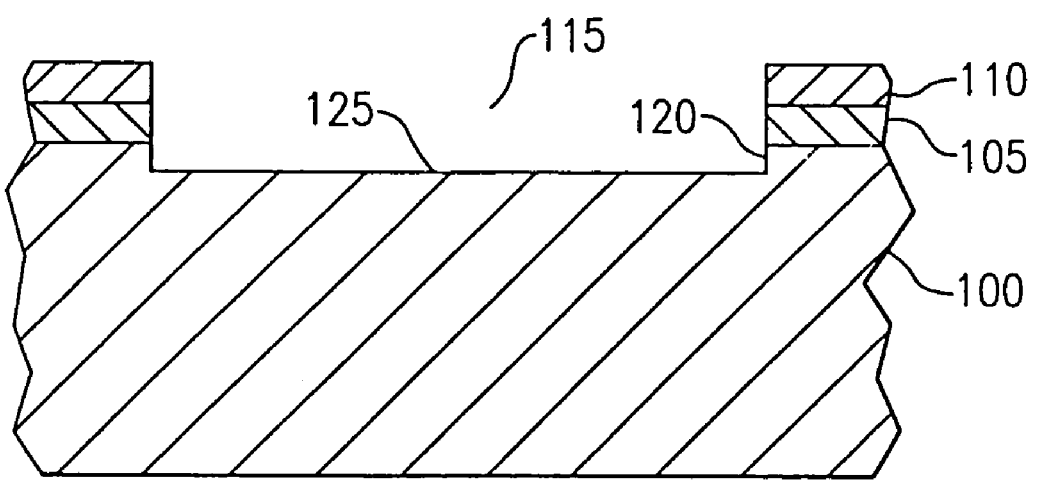

FIG. 1D shows the result of subsequent oxide etching using a process that is designed for etching silicon oxide. Precise knowledge of the oxide film 105 thickness is crucial so as to avoid appreciable etching into the underlying silicon substrate 100. Lastly, (FIG. 1E), the desired etch depth 120 into the silicon substrate 100 is achieved by performing an etch of the silicon using the oxide etch process for etch rate control. The ultra-shallow channel 125 is thus formed in the silicon substrate 100. As with virtually all etch processes, exact etch rates will commonly depend on percent area of the substrate that is being etched. The rate should be established in advance by etch experiments on similarly patterned substrates.

Figure 2A:
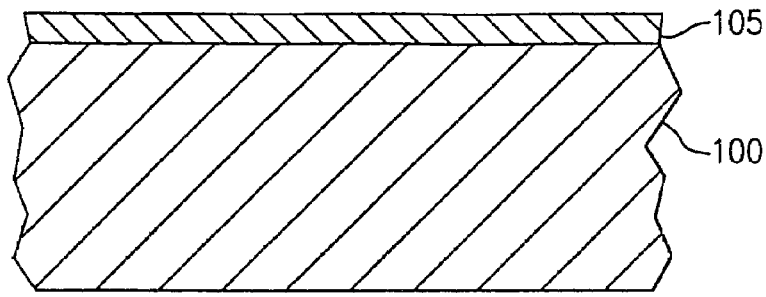
FIGS. 2A–2D show cross-sectional views of a process sequence that was followed to produce ultra-shallow channels according to an embodiment of the invention.
Figure 2B:
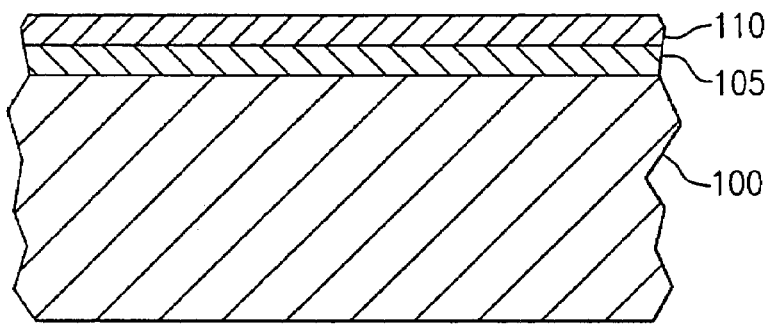
Figure 2C:
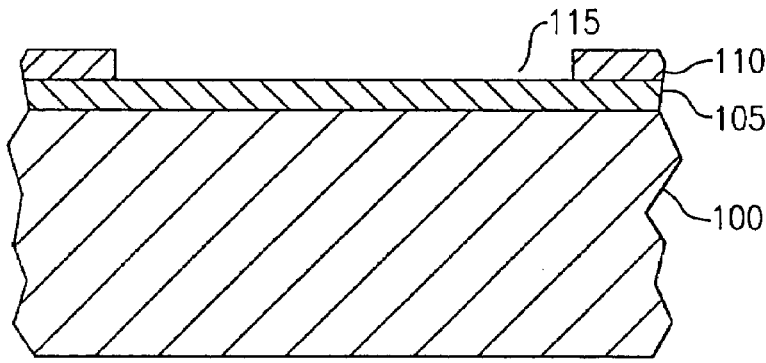
Figure 2D:
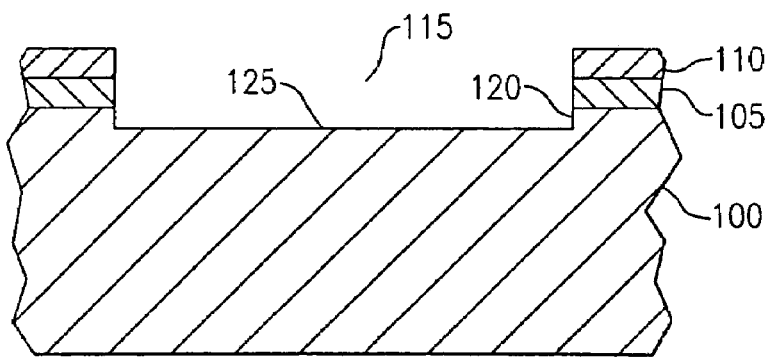

In an alternative embodiment, as shown in FIGS. 2A–2D, the two consecutive etches using an oxide etch process may be combined into a single etch so long as oxide and silicon etch rates are precisely known. FIGS. 2A–2C, respectively, show cross-sectional views of the silicon substrate 100 after growth/deposition of silicon oxide 105, after deposition/coating of photoresist 110, and after patterning of the photoresist to create an opening 115. FIG. 2D shows the result of the single etch through oxide 105 and into silicon 100. The targeted etch depth 120 is achieved by etching for a time given as:

Time=(target depth into silicon substrate 120)/(silicon etch rate in oxide etch)+(oxide film 105 thickness)/(oxide etch rate in oxide etch)

Figure 3A:
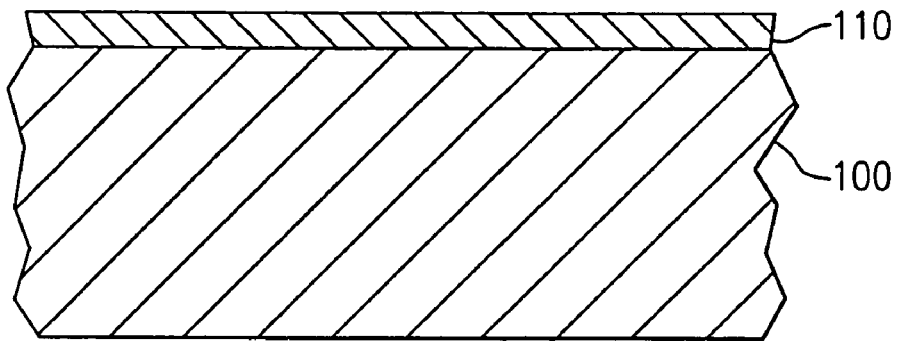
FIGS. 3A–3C show cross-sectional views of a process sequence that was followed to produce ultra-shallow channels according to an embodiment of the invention.
Figure 3B:
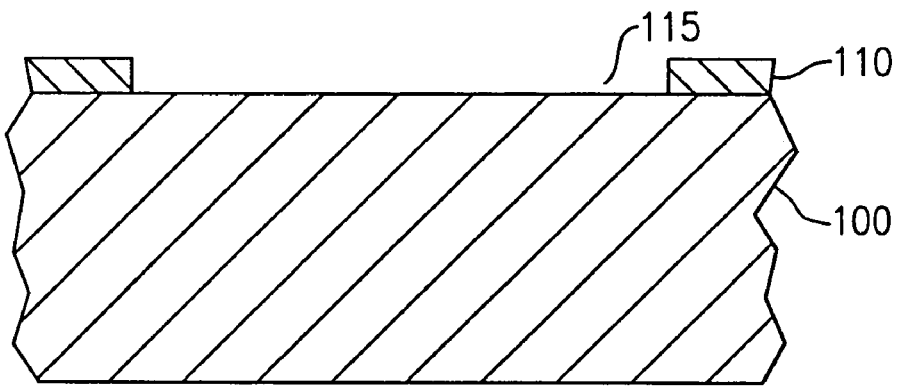
Figure 3C:
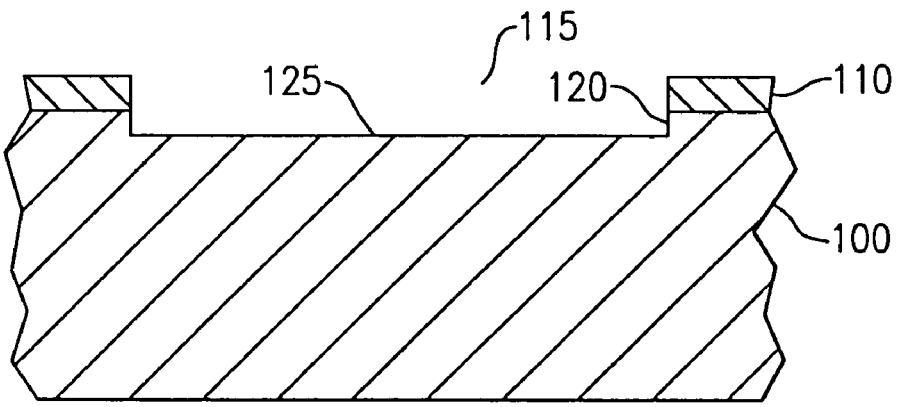

In an alternative embodiment (FIGS. 3A–3C) the photoresist 110 maybe patterned directly on the silicon substrate 100, thereby eliminating the need for an oxide film. FIGS. 3A–3C, respectively, show cross-sectional views of the silicon substrate 100 after coating of photoresist 110, after patterning of photoresist 110 to create an opening 115, and after etching of the silicon substrate 100 to the desired etch depth 120. This runs counter to standard photolithographic practice, however, inasmuch as pattern definition of photoresist is generally more problematic when done directly on silicon as compared to being done on an oxide film. Small, micrometer-size features are particularly difficult to accurately define in this case when using a g-line (436.5 nm) illumination light source.

The preferred embodiment is preferable to the latter alternative embodiment for several reasons. First, more precise patterning of small features is obtained on an oxide film as opposed to a bare silicon substrate, as discussed previously. Secondly, the amount of silicon etching is ultimately limited by the amount of available masking material—silicon oxide, photoresist, or both. The preferred embodiment would permit more extensive etching of silicon if needed because the oxide mask would persist through some additional etching after the photoresist mask was consumed.

Figure 4:
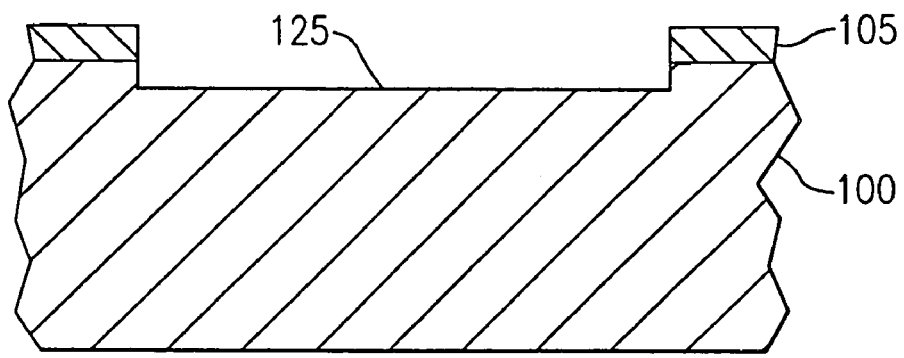
FIG. 4 shows an optional step in the process sequence according to the embodiment of FIGS. 3A–3C.
Figure 5:
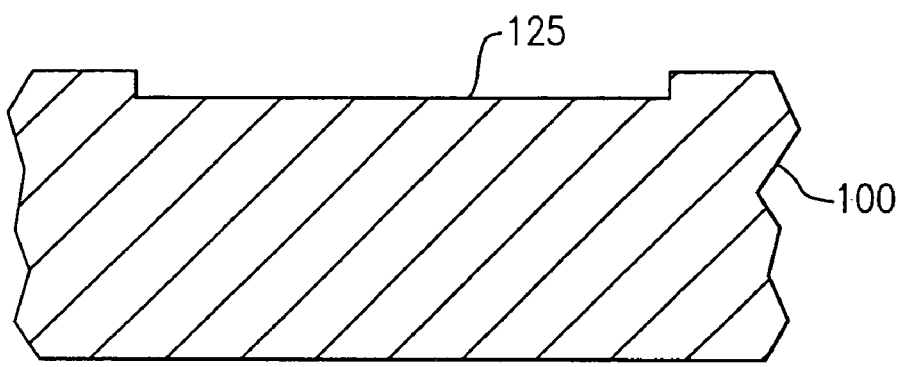
FIG. 5 shows an optional step in the process sequence according to the embodiment of FIGS. 3A–3C.

After formation of the shallow fluid channel 125 as described in FIGS. 1A–1E, the photoresist film 110 may be removed in an oxygen plasma (FIG. 4), and subsequent processing steps can be followed to produce additional features and/or enhance the device's functionality. For example, as shown in FIG. 5, the remaining oxide mask layer 105 from FIG. 4 can be removed in a hydrofluoric acid-based solution, leaving the ultra-shallow channel 125 in the silicon substrate 100.

Figure 6:
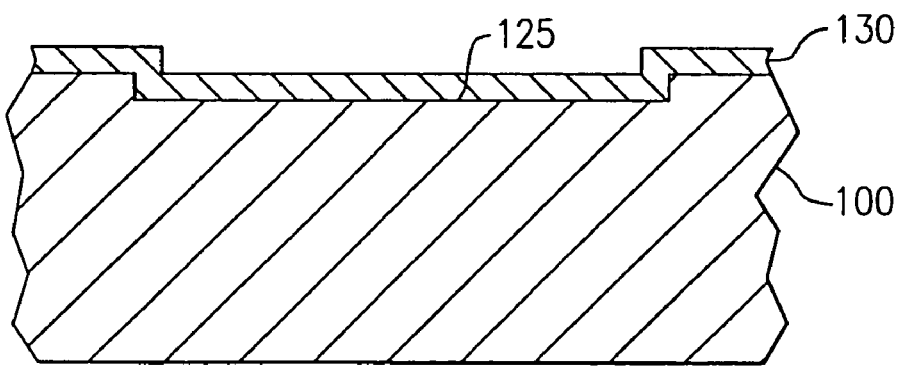
FIG. 6 shows a cross-sectional view of a channel that has been passivated by growth or deposition of a passivating film.

Fluidic channels or other features that have been fabricated in silicon by the disclosed method can be passivated if desired for purposes of electrical or chemical isolation by subsequent thermal growth of silicon oxide or by conformal deposition of silicon oxide or silicon nitride. These processes will preserve the depth of the channel relative to the surrounding field region. FIG. 6 shows a cross-sectional view of a channel 125 that has been passivated by growth or deposition of a passivating film 130 such as thermal oxide, LPCVD silicon oxide, LPCVD silicon nitride, PECVD silicon oxide, or PECVD silicon nitride.

FIGS. 7A–7D show a series of cross-sectional views of a process sequence of yet another alternative embodiment relying on the same principle of using a highly selective etch to etch the material to which the etch is selective at a low, reproducible rate which can be used to form ultra-shallow channels in oxide. That is, a silicon etch can be used to create extremely shallow channels in silicon oxide, using photoresist as a mask. Given a silicon:oxide etch rate selectivity of 150:1, oxide etch rates of 10 nm/min are easily achieved, thereby allowing etch depth precision on the order of 5 nm.

Figure 7A:
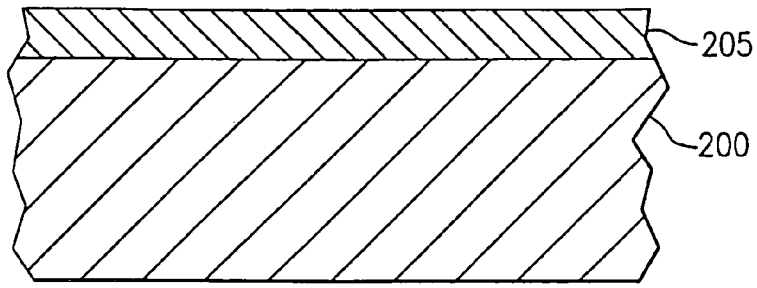
FIGS. 7A–7D show a series of cross-sectional views of a process sequence of yet another alternative embodiment.
Figure 7B:
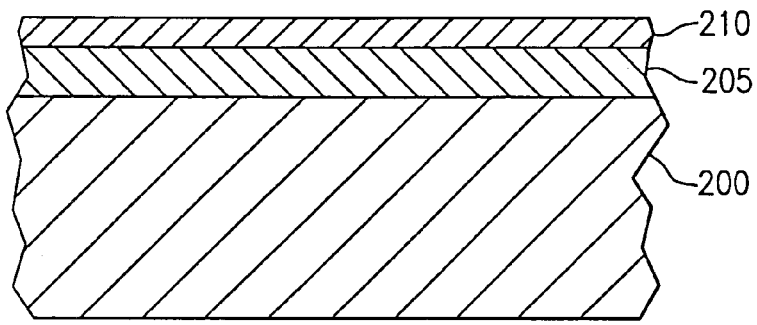
Figure 7C:
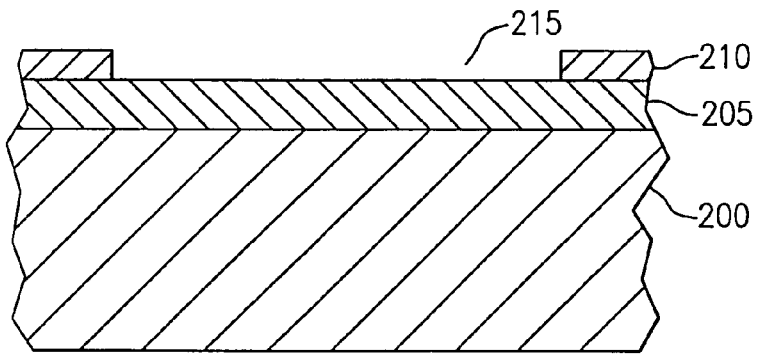
Figure 7D:
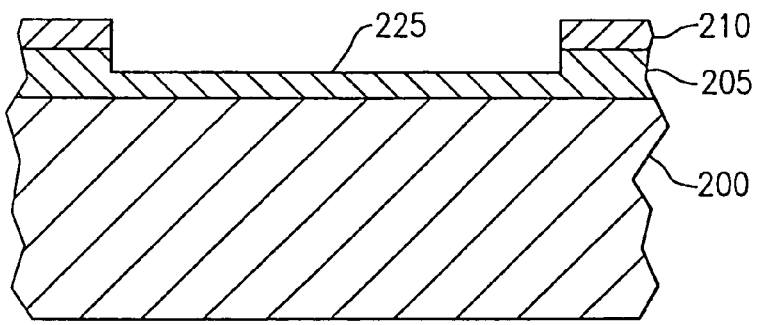

FIG. 7A shows a silicon substrate 200 on which a silicon oxide film 205 has been grown or deposited. Next, a film of photoresist 210 is coated on the oxide layer 205 (FIG. 7B) after which the photoresist layer 210 is patterned lithographically to create openings 215 to the underlying oxide layer 205 (FIG. 7C). The exposed oxide areas 215 are then etched using the silicon etch to create the required channel 225 (FIG. 7D).

The ultra-shallow fluidic channels or structures so formed—whether passivated or unpassivated—are compatible with a variety of bonding methods for purposes of providing a necessary containing surface for the channels.

Figure 8A:
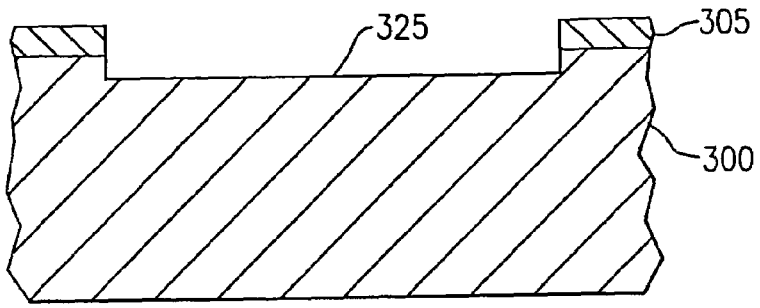
FIGS. 8A–8C show a progression of cross-sectional views leading to the creation of damascene structures using the disclosed etch method of shallow-ultra-shallow channel formation taught herein to etch structures other than fluidic channels.
Figure 8B:
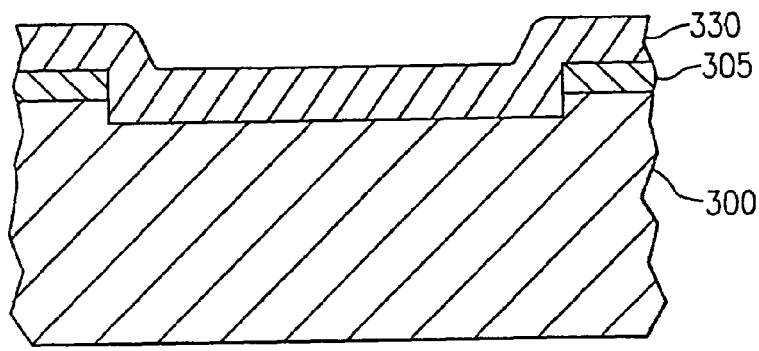
Figure 8C:
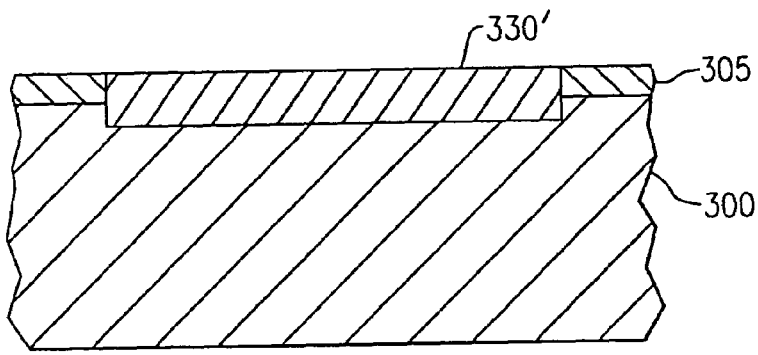
Figure 9:
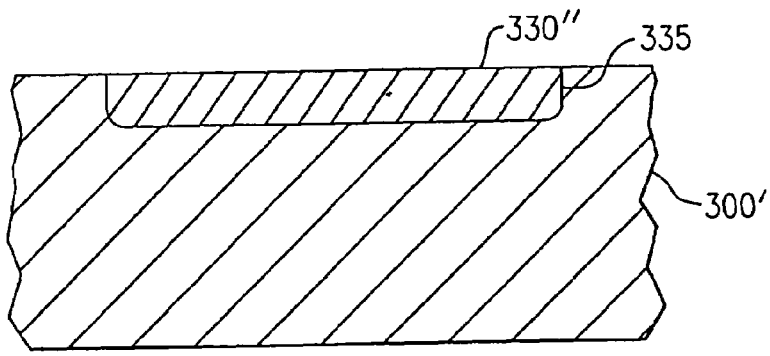
FIG. 9 shows an example of how inlaid material is determined by the depth of the ultra-shallow etch.

FIGS. 8A–8C show a progression of cross-sectional views leading to the creation of damascene structures using the disclosed etch method of shallow-ultra-shallow channel formation taught herein to etch structures other than fluidic channels. FIG. 8A shows the silicon substrate 300 and oxide mask 305 after etching of the ultra-shallow channel 325. Next, a material 330 may be deposited (FIG. 8B), followed by chemical-mechanical polishing (CMP) to finish with an inlaid island of material 330', as shown in FIG. 8C. The top of the inlaid material 330' is coplanar with the top of the remaining oxide layer 305, thereby facilitating subsequent patterning processes. FIG. 9 shows an example 335 of how the inlaid material 330" is determined by the depth of the ultra-shallow etch. In this case, the oxide layer 305 of FIG. 8A would have been removed prior to deposition of material 330".

Stepped Fluidic Channels—Methods of Fabrication

Fluidic channels having two or more segments with intentionally different depths may be desired for a variety of purposes. Mixing of two or more fluids may be aided by disruption of an otherwise smooth, continuous flow path. Filtering of relatively large particles or precipitates may be effectively accomplished by constricting the fluid flow path in a vertical (or horizontal) dimension. Resolution of depth or volume-dependent analysis techniques directed at fluid in a channel can be improved in terms of signal-to-noise ratio by reducing the depth of the fluid in a detection/analysis region of the channel.

Figure 10A:
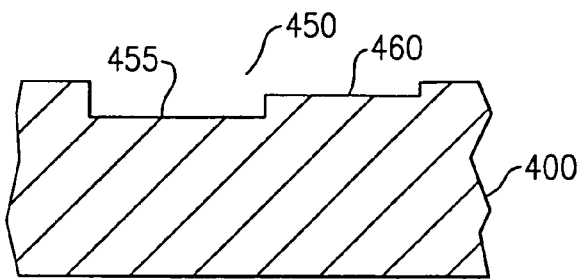
FIGS. 10A–10D show a channel with cross-sectional profiles desired for various applications.
Figure 10B:
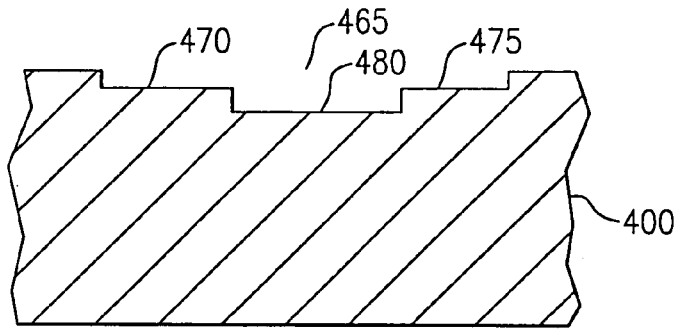
Figure 10C:
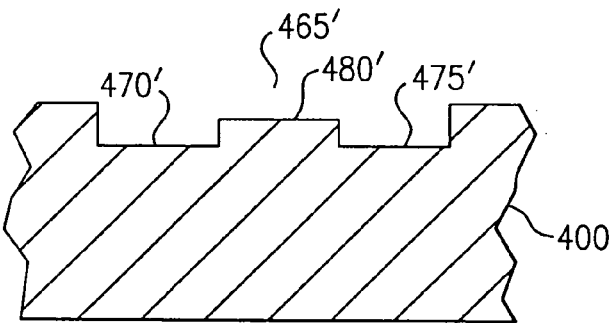
Figure 10D:
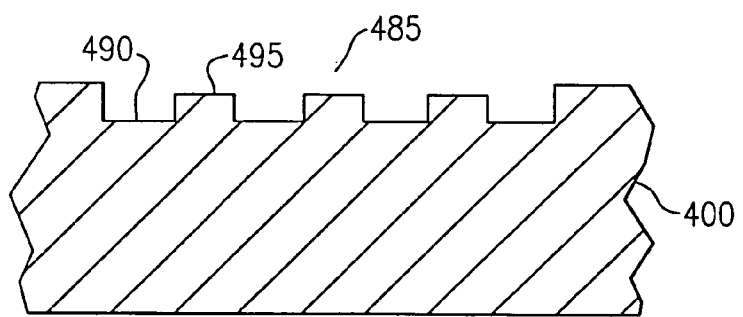

For the foregoing application and others, then, a channel with cross-sectional profiles like those shown in FIGS. 10A–10D, for example, is desired. FIG. 10A shows a cross-sectional view of a two-segment channel 450, a first segment 455 being etched to a greater depth than a second segment 460 in the substrate 400. FIG. 10B shows a three-segment channel 465, in which the first 470 and third 475 segments are etched to one depth and the second 480 segment is etched to a different, greater depth. FIG. 10C shows a three-segment channel 465', in which the first 470' and third 475' segments are etched to one depth and the second 480' segment is etched to a different, lesser depth. FIG. 10D shows a multiple-segment channel 485, alternating between deeper 490 and shallower 495 etch depths. Discrete steps in channel depth cannot be produced through a standard, single pattern-and-etch sequence. To first order, all areas open to the etching plasma will etch to approximately the same depth.

Figure 11A:
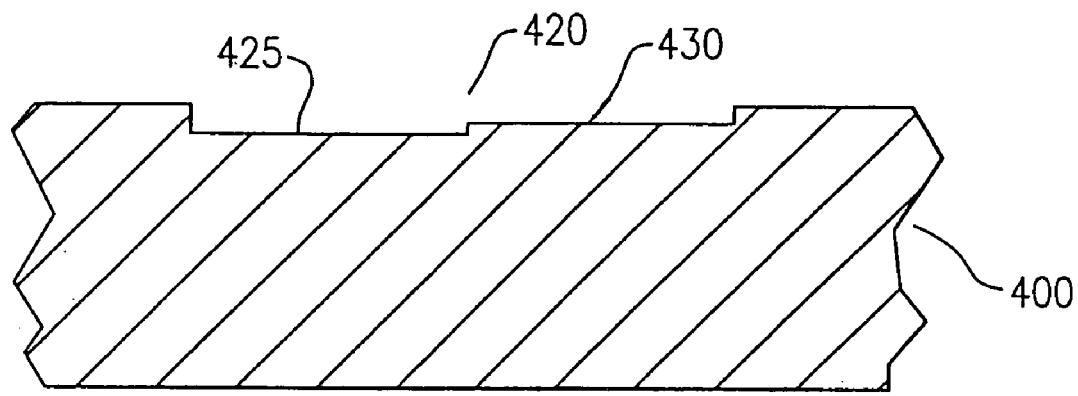
FIG. 11A shows a two-segment channel with two ultra-shallow segments formed according to the first principal aspect of the invention.
Figure 11B:
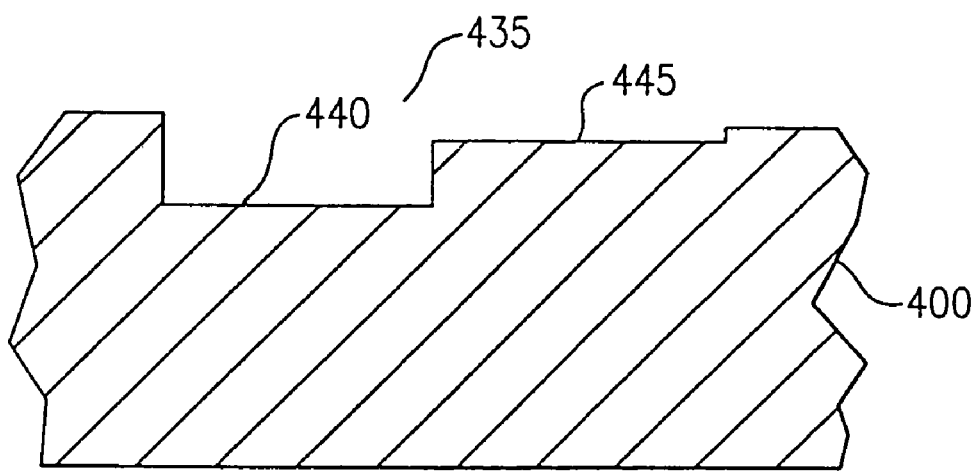
FIG. 11B shows a two-segment channel with a segment of conventional depth and a ultra-shallow segment formed according to the first principal aspect of the invention.

The present invention discloses process methods whereby stepped ultra-shallow channels can be fabricated. These stepped channels can be combinations of two or more different ultra-shallow depths or, alternatively, combinations of one or more conventional channel depths with one or more ultra-shallow depths. FIG. 11A shows a two-segment channel 420 comprising two ultra-shallow segments 425 and 430. FIG. 11B shows a two-segment channel 435 comprising a segment of conventional depth 440 and a ultra-shallow segment 445. Formation of the ultra-shallow segments 425, 430, and 445 relies on the first principal aspect of the present invention, as discussed previously.

Figure 12A:
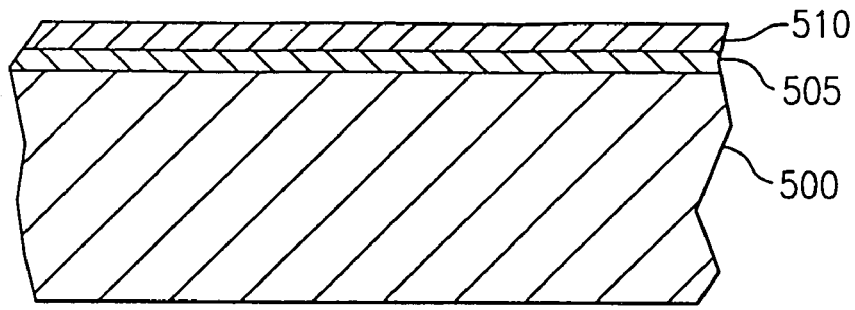
FIGS. 12A–12F show the process sequence for fabrication of a stepped fluidic channel which has two ultra-shallow segments.
Figure 12B:
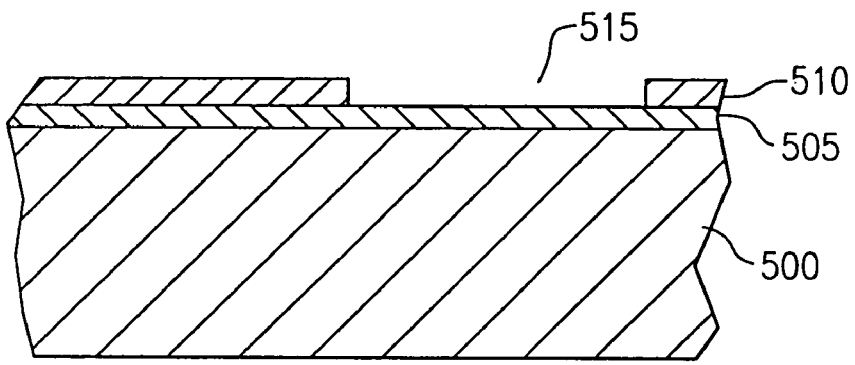
Figure 12C:
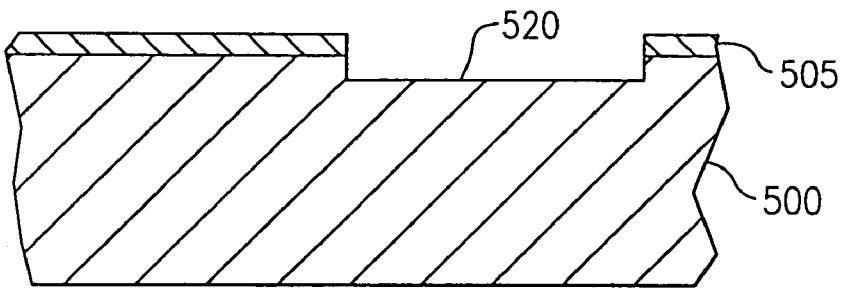
Figure 12D:
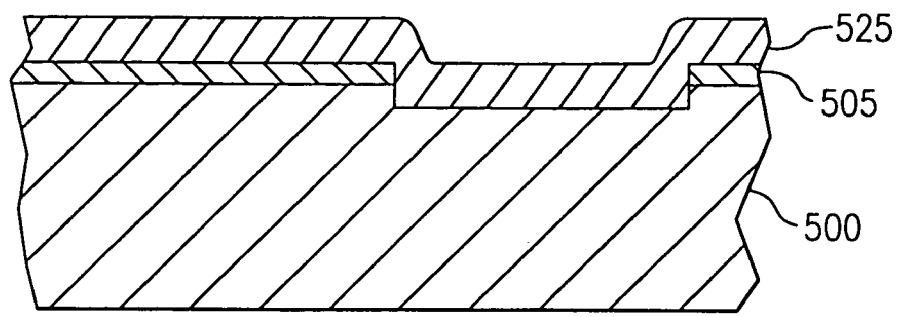
Figure 12E:
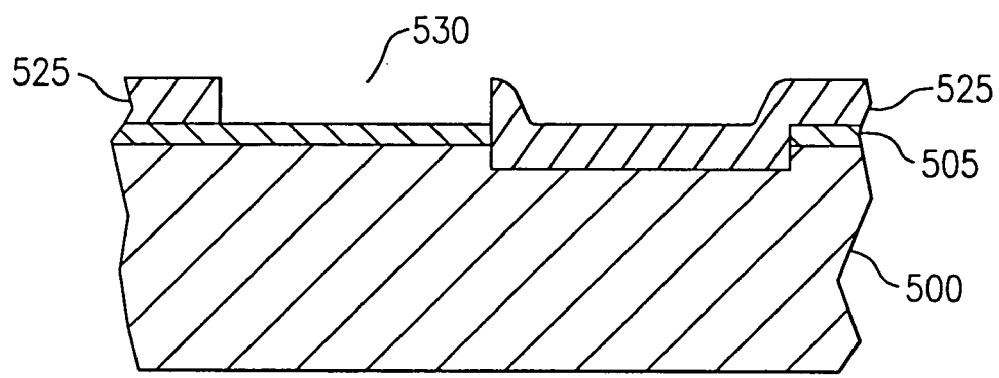
Figure 12F:
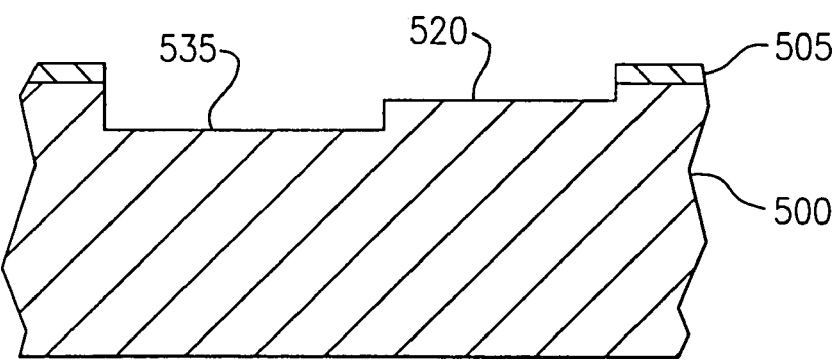
Figure 13:
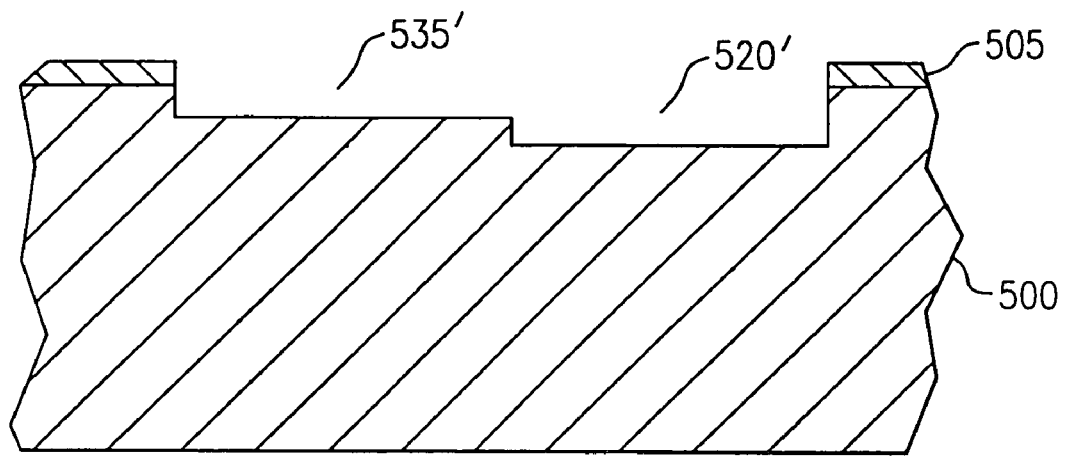
FIG. 13 shows an alternative to the channel shown in FIGS. 12A–12F, in which the second ultra-shallow segment is etched to a shallower depth than the first ultra-shallow segment.

The process sequence for fabrication of a stepped fluidic channel comprising two ultra-shallow segments is shown in FIGS. 12A–12F. FIG. 12A shows a cross-sectional view of a silicon substrate 500 on which has been grown or deposited a silicon oxide layer 505 and, additionally, on which has been coated a photoresist layer 510. In FIG. 12B, the photoresist layer 510 has been lithographically patterned to create an opening 515 to the underlying oxide layer 505. FIG. 12C shows the result from subsequently practicing the etch method taught as the first principal aspect of the present invention to create a ultra-shallow channel segment 520, followed by removal of the photoresist layer. In FIG. 12D, a second layer of photoresist 525 has been coated. FIG. 12E shows the result of lithographically patterning the photoresist layer 525 to create an opening 530 to the underlying oxide layer 505. Lastly, FIG. 12F shows the result of practicing the etch method taught as the first principal aspect of the present invention to create a second ultra-shallow channel segment 535, followed by removal of the photoresist layer. In this example, the second ultra-shallow segment 535 is etched to a greater depth than the first ultra-shallow segment 520. Alternatively, as shown in FIG. 13, the second ultra-shallow segment 535' may be etched to a shallower depth than the first ultra-shallow segment 520'.

Extension of the process method to fabrication of a fluidic channel with more than two discrete depths will be obvious to skilled practitioners of the art, each separate etch depth requiring its own lithographic patterning and etch.

Figure 14:
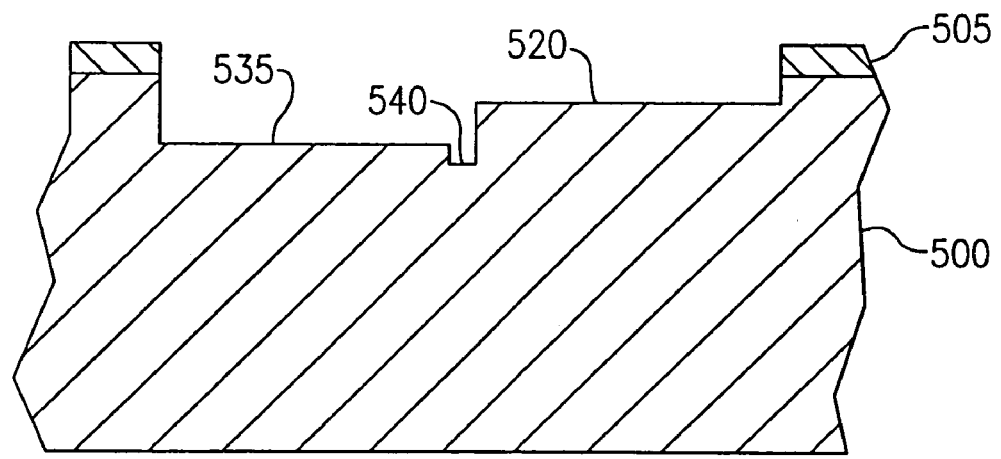
FIG. 14 shows an exaggerated cross-sectional view of an etch trough at the connection point of two channel segments.

Mask-to-mask (mis)alignment will inevitably lead to small regions of overlap between adjacent channel segments. In normal processing, this would mean that the region of overlap would be etched to a depth representative of the summation of the two adjacent segments, to first order. This may be acceptable for many applications, and may, in fact, be desirable for mixing purposes, the trough thereby created causing disordered flow (mixing). FIG. 14 shows an exaggerated cross-sectional view of such an etch trough 540 at the connection point of two channel segments 520 and 535. Alternatively, the etch trough in the region of pattern overlap between adjacent channel segments may be avoided by several means.

The use of the latent masking process methodology, as described below, will prevent the creation of the etch trough because that methodology is inherently a self-aligned patterning scheme. That is, there is no overlap of adjacent patterns because one pattern (the one corresponding to the deeper channel segment) is a proper subset of the entire channel pattern. The problematic overlap only arises when adjacent segments are separately and distinctly patterned.

As in the case of the first principal aspect of the present invention—formation of a ultra-shallow fluidic channel having a single, uniform depth—the depths of the shallow-ultra-shallow segments of a stepped channel are limited only by persistence of masking material (photoresist). Typically, photoresist:oxide selectivities are on the order of 1:1, placing a practical limit of roughly the smallest feature size on etch depth (since coated photoresist thickness is generally held to less than or approximately equal to the smallest feature's dimension).

For channels other than those of ultra-shallow depth, the formation of stepped channels may be problematic due to difficulties inherent in coating/spinning photoresist over etched features having greater than approximately one-micrometer height or depth. Topographical discontinuities can cause coating defects, compromising attempts to perform subsequent patterning steps with fidelity to the intended design. There are several methods by which this obstacle may be overcome.

U.S. patent application Ser. No. 09/334,408 (Moon et al.) describes improved process methods for fabricating MEMS and microfluidic devices. In that application, methods denoted as SMILE (for simultaneous multi-level etching) and latent masking are disclosed as means for surmounting common constraints that inhibit or prevent multi-level patterning of a surface due to interference of etched topography with subsequent photoresist spinning. The inventions disclosed in the Ser. No. 09/334,408 application provide enhanced design flexibility and improved manufacturability for MEMS and microfluidic devices. Reference is made to U.S. patent application Ser. No. 09/334,408, which is incorporated herein by reference as though fully set forth in its entirety, for a more detailed explanation of the SMILE process.

The SMILE process methodology was developed specifically for the purpose of overcoming patterning difficulties due to topographical discontinuities. In the present context of microfluidic channels, FIGS. 15A–15H show a progression of cross-sectional views of the fabrication of a two-segment channel. The salient characteristic of SMILE processing is the creation of a first pattern (corresponding to a first channel segment) in the silicon oxide mask, followed by re-coating of photoresist and patterning of the photoresist with both the original pattern as well as a second pattern (corresponding to a second channel segment). The first pattern, being open to the silicon, may then be etched to a certain depth, followed by oxide mask etching to open the second pattern, then etching both patterns to targeted depths. In this case, the first pattern would be the segment with the greater (deeper) targeted depth, and the amount of the initial etch would be offset from the final depth target by the amount of the second targeted depth.

Figure 15A:
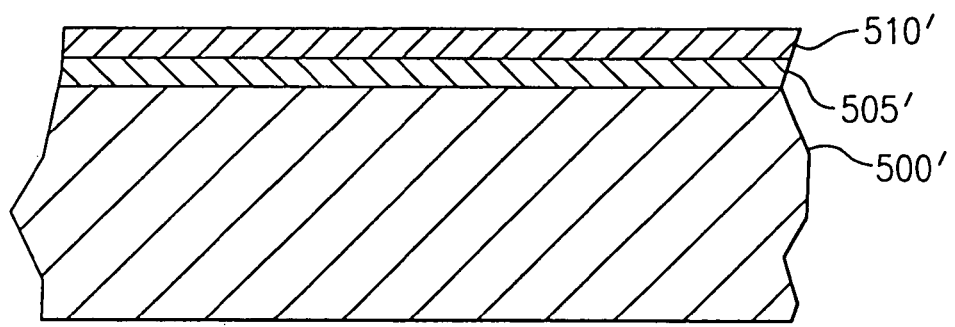
FIGS. 15A–15H show a progression of cross-sectional views of the fabrication of a two-segment channel according to an embodiment of the invention using SMILE methodology.
Figure 15B:
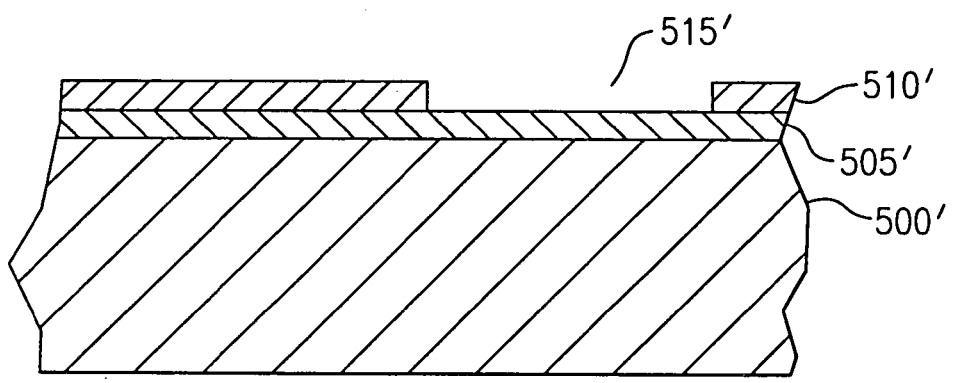
Figure 15C:
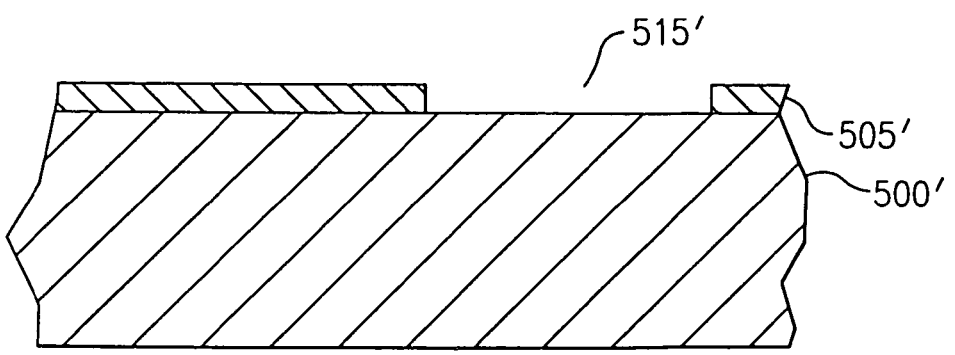
Figure 15D:
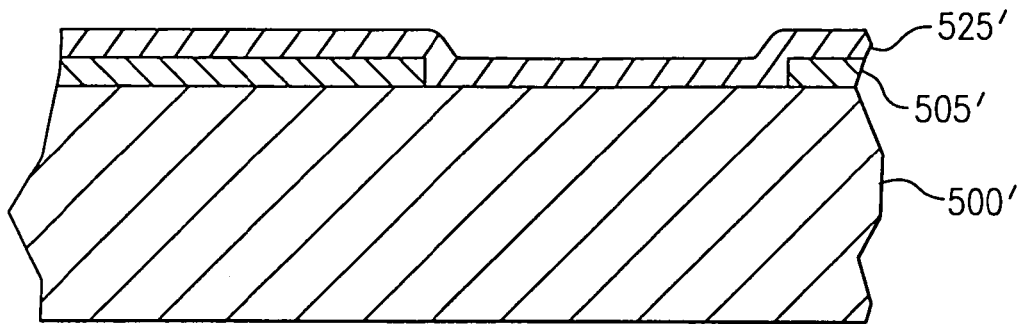
Figure 15E:
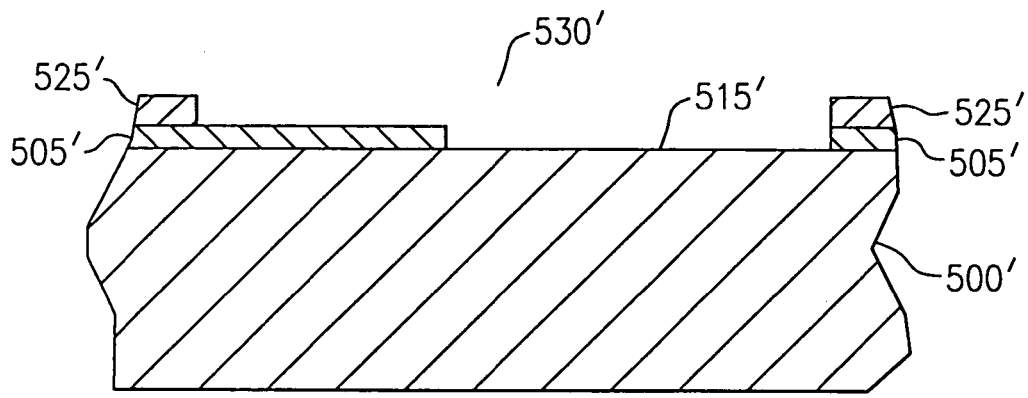
Figure 15F:
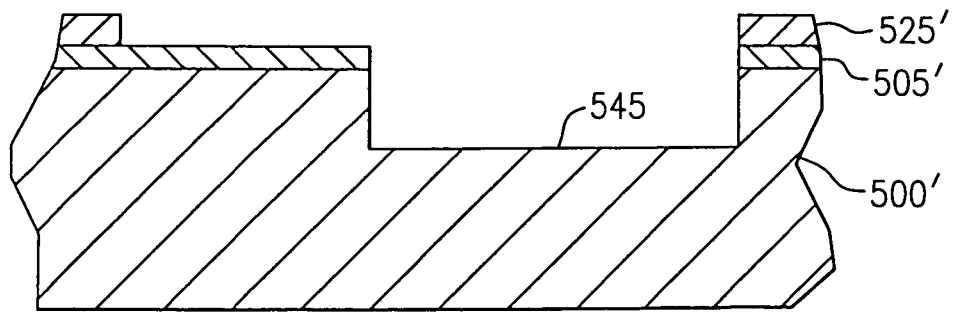
Figure 15G:
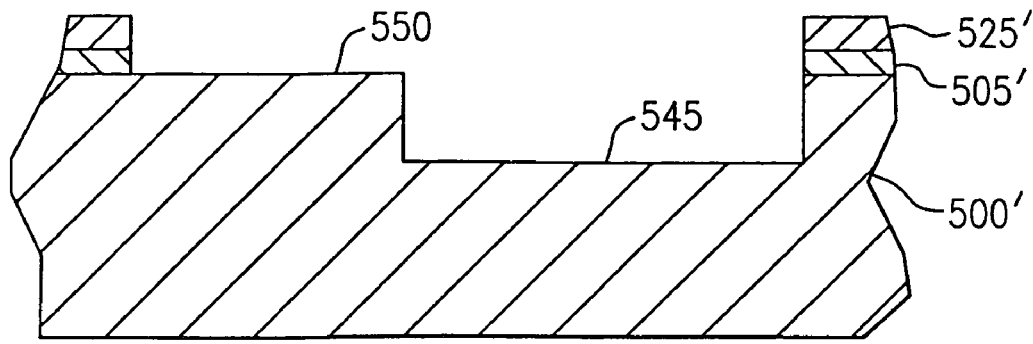
Figure 15H:
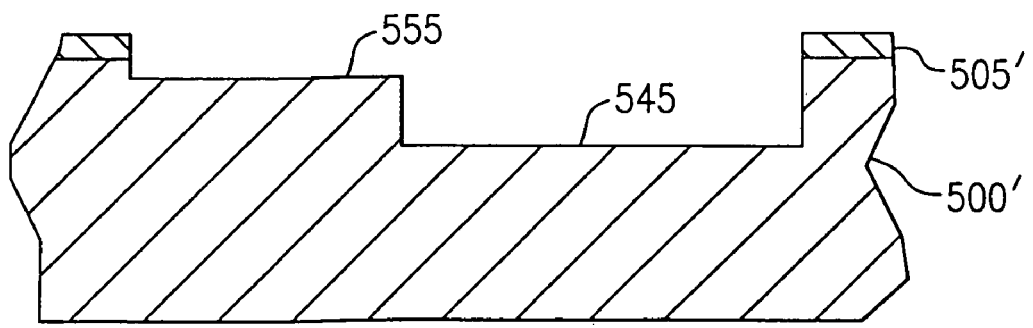

FIG. 15A shows a cross-sectional view of a silicon substrate 500' on which has been grown or deposited a silicon oxide layer 505' and, additionally, on which has been coated a photoresist layer 510'. In FIG. 15B, the photoresist layer 510' has been lithographically patterned to create an opening 515' to the underlying oxide layer 505'. FIG. 15C shows the resulting cross-sectional view after the oxide layer 505' has been etched in opening 515' to reach the underlying silicon substrate 500' and the photoresist has been removed. Next, a second photoresist layer 525' is coated uniformly over the substrate 500' and overlying layers (FIG. 15D), after which the photoresist layer 525' is lithographically patterned to create an opening 530' to the underlying oxide layer 505' and the silicon substrate 500' (FIG. 15E). Using the oxide 505' and remaining photoresist layer 525' as a mask, an etch of the exposed silicon substrate area 515' is performed. This etch can be done using the method taught in the first aspect of the present invention to form a ultra-shallow channel segment 545. Alternatively, a normal silicon etch can be performed to form a deep channel. FIG. 15F shows the wafer after the first channel segment 545 has been etched. FIG. 15G shows the result after next etching the oxide layer 505' to the underlying silicon substrate 500' in the area 550 of the second channel segment. Finally, as shown in FIG. 15H, the second channel segment 555 is etched and any remaining photoresist is removed. The second channel segment 555 may be etched to either ultra-shallow depth using the method taught in the first principal aspect of the present invention or to conventional depth using a standard silicon etch process. It is evident that, in this method, the first etched channel segment 545 will be deeper than the second etched channel segment 555.

Latent masking is conceptually similar to the SMILE methodology, essentially reversing the order of pattern etching from the previous (SMILE) example. In this case, an initial patterning of both channel segments would be done and etched into the underlying silicon oxide layer, stopping at the oxide/silicon interface. A second patterning is then done, coating photoresist and patterning it so as to create openings corresponding to a first channel segment. The first segment is etched into silicon to a certain depth, after which the photoresist is removed. The remaining oxide mask is then used to mask a second etch which is stopped when targeted etch depths are achieved. As in the case of SMILE processing, the first segment would be the segment with the greater depth target. The amount of the initial etch would be offset from the final etch depth target by the amount of the second targeted depth.

Figure 16A:
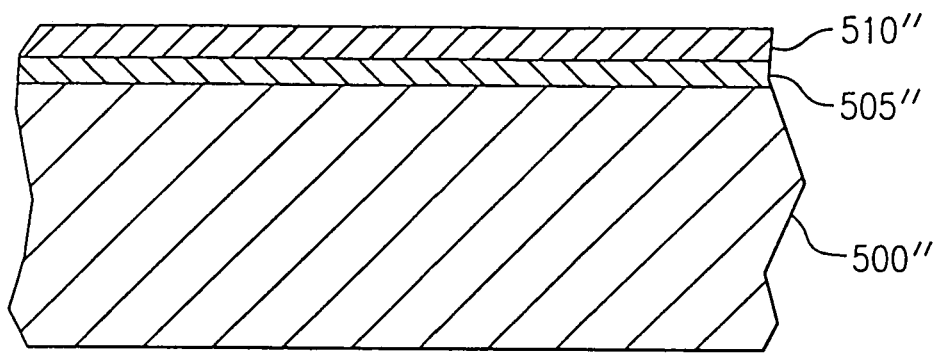
FIGS. 16A–16G show cross-sectional views of a process sequence that follows latent masking methodology.
Figure 16B:
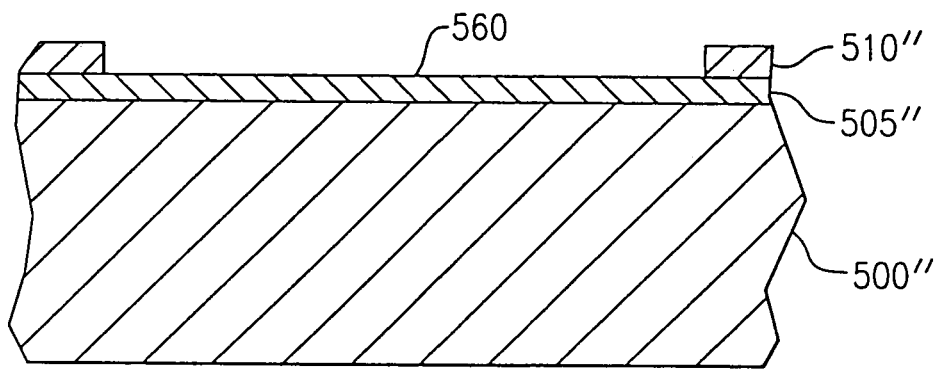
Figure 16C:
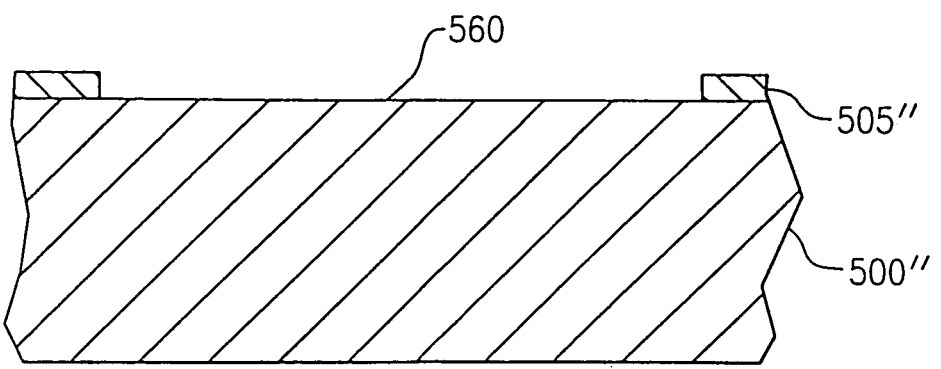
Figure 16D:
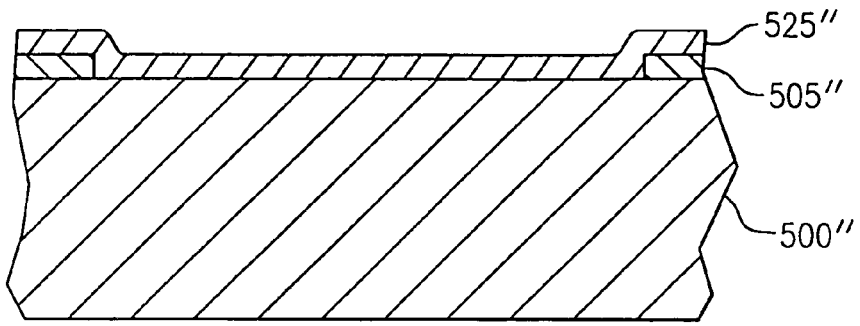
Figure 16E:
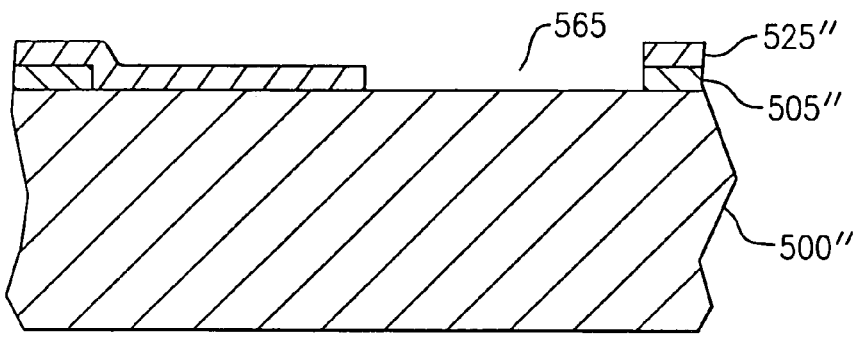
Figure 16F:
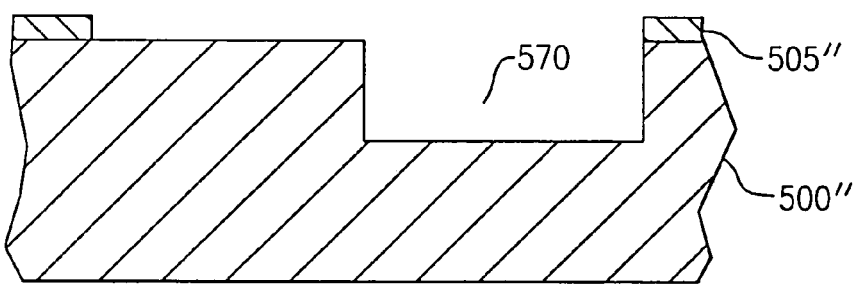
Figure 16G:
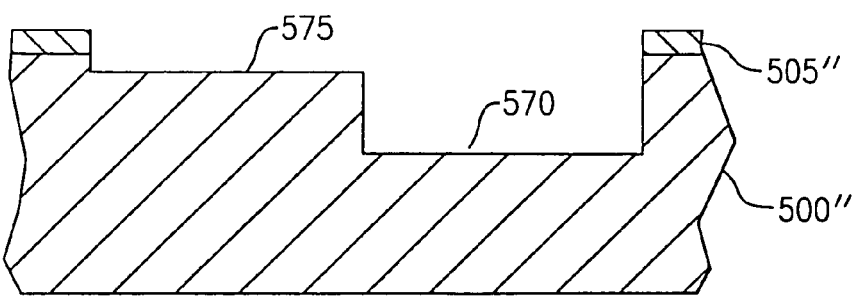

FIGS. 16A–16G show cross-sectional views of a process sequence that follows the latent masking methodology. FIG. 16A shows a cross-sectional view of a silicon substrate 500" on which has been grown or deposited a silicon oxide layer 505" and, additionally, on which has been coated a photoresist layer 510". In FIG. 16B, the photoresist layer 510" has been lithographically patterned to create an opening 560 to the underlying oxide layer 505". In this methodology, the opening 560 would correspond to the entire channel, rather than a single segment as in the SMILE methodology. FIG. 16C shows the resulting cross-sectional view after the oxide layer 505" has been etched in opening 560 to reach the underlying silicon substrate 500" and the photoresist has been removed. Next, a second photoresist layer 525" is coated uniformly over the substrate 500" and overlying patterned oxide layer 505" (FIG. 16D), after which the photoresist layer 525" is lithographically patterned to create an opening 565 to the underlying silicon substrate 500" corresponding to a first channel segment (FIG. 16E). Using the photoresist layer 525" as a mask, an etch of the exposed silicon substrate 500" is performed. This etch can be done using the method taught in the first aspect of the present invention to form a ultra-shallow channel segment 570. Alternatively, a normal silicon etch can be performed to form a deep channel. FIG. 16F shows the wafer after the first channel segment 570 has been etched into the silicon substrate 500" and any remaining photoresist has been removed. Finally, as shown in FIG. 16G, the second channel segment 575 is etched into the silicon substrate 500". The second channel segment 575 may be etched to either ultra-shallow depth using the method taught in the first principal aspect of the present invention or to conventional depth using a standard silicon etch process. It is evident that the first etched channel segment 570 will again be deeper than the second etched channel segment 575.

In an alternative embodiment of the present invention, etch depth may be varied continuously, rather than discretely, by taking advantage of the etch lag effect. This effect, arising from steadily increasing difficulty in getting reactive species into and etch by-products out of high-aspect-ratio features, is manifested as a monotonically decreasing etch depth as the lateral dimension of the etch pattern is decreased. If the device's required functionality, then, is compatible with flexibility in layout design, the depth of the fluid channel can be increased (decreased) by increasing (decreasing) the width of the channel as seen in plan and cross-sectional views in FIGS. 17A and 17B. It is further noted that this effect may be obtained, not only in single-segment fluid channels, but in any or all parts of multi-segment channels as well.

Figure 17A:
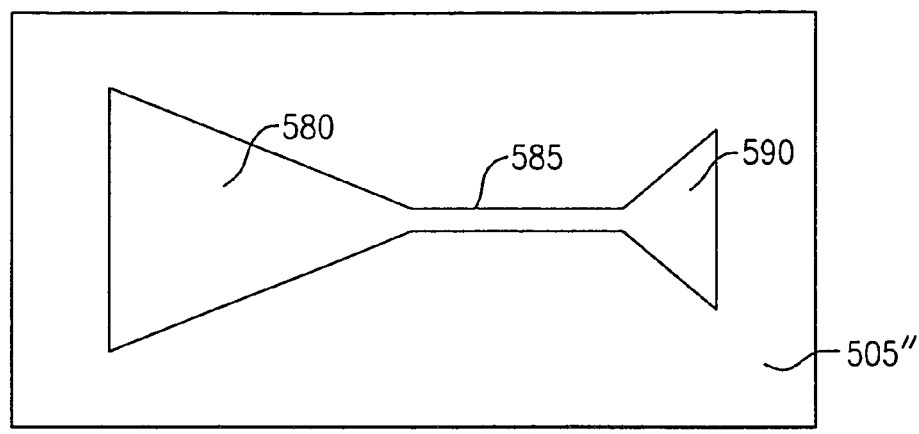
FIG. 17A shows a plan view of a fluidic channel with three segments of varying lateral dimensions formed by an embodiment of the present invention.
Figure 17B:
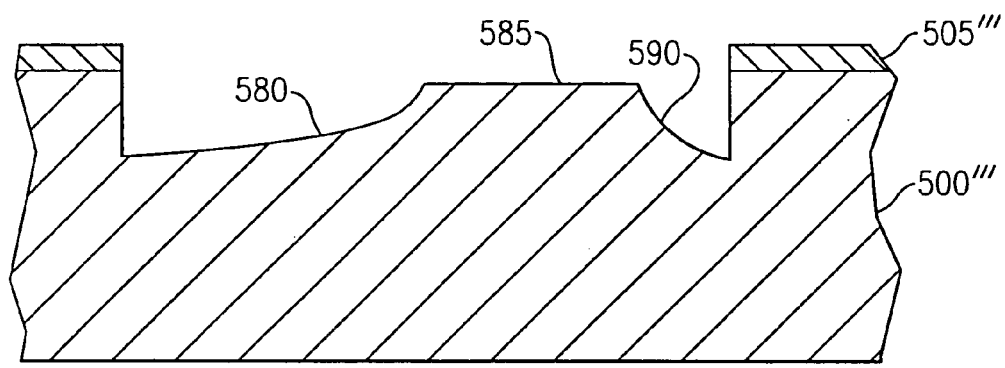
FIG. 17B shows a cross-sectional view of the fluidic channel of FIG. 17A.

FIG. 17A shows a plan view of a fluidic channel comprising three segments 580, 585, and 590. The salient characteristics of segments 580 and 590 are the variations in designed lateral dimension, with segment 580 narrowing from left to right and segment 590 broadening from left to right. The designed lateral dimension of the middle segment 585 is constant and equal to the smallest lateral dimension in segments 580 and 590. The effect of the intentionally varied lateral dimensions is shown in cross-sectional view in FIG. 17B. FIG. 17B shows the resulting channel segments 580, 585, and 590 after completion of etching into the silicon substrate 500'''. It is to be noted that, where lateral dimensions decrease, the effect of etch lag is to diminish the final etched depth of the channel. Specifically, the etched depth is least in the relatively narrow middle segment 585, with etched depth in segments 580 and 590 decreasing as the corresponding lateral dimension decreases.

Figure 18A:
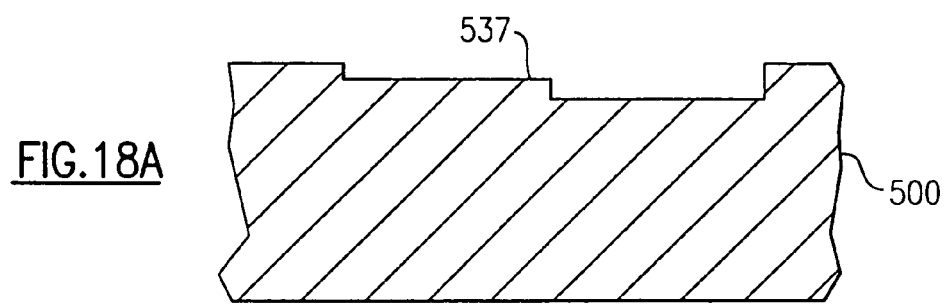
FIG. 18A shows a cross-sectional view of a channel as etched into a silicon substrate after removal of masking oxide.
Figure 18B:
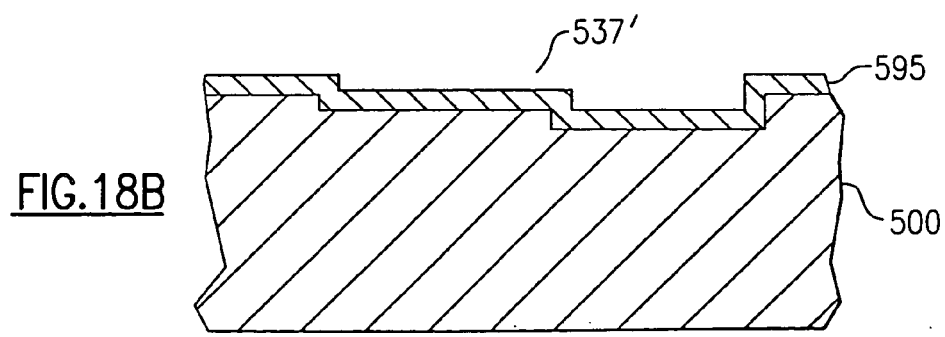
FIG. 18B shows the resulting channel from FIG. 18A after conformal growth or deposition of a passivating film.

As in the case of channels and/or structures of ultra-shallow depth, the surfaces of stepped channels may be passivated by thermal growth of silicon oxide or by the deposition of a passivating film like silicon oxide or silicon nitride. These processes will preserve the depth of the channel relative to the surrounding field region provided that any remaining masking oxide is removed prior to the growth or deposition. FIG. 18A shows a cross-sectional view of a channel 537 as etched into the silicon substrate 500 after removal of masking oxide. FIG. 18B shows the resulting channel 537' after conformal growth or deposition of a passivating film 595 such as thermal oxide, LPCVD silicon oxide, LPCVD silicon nitride, PECVD silicon oxide, or PECVD silicon nitride.

The stepped ultra-shallow fluidic channels or structures so formed—whether passivated or unpassivated—are compatible with a variety of bonding methods for purposes of providing a necessary containing surface for the channels.

Structures in Fluidic Channels—Methods of Fabrication

Figure 19A:
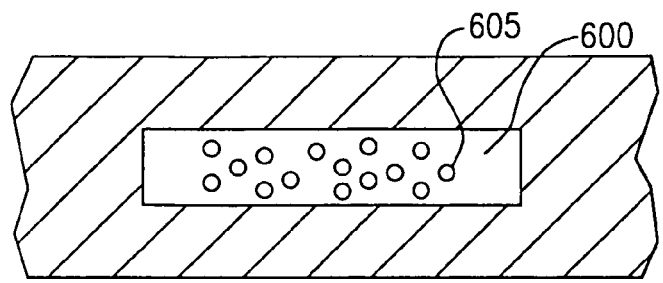
FIG. 19A shows a plan view of a channel that is populated with posts.
Figure 19B:
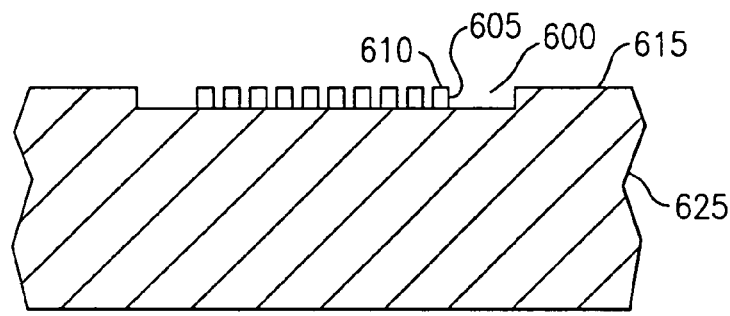
FIG. 19B shows a cross-sectional view of the channel of FIG. 19A after etching is completed.
Figure 19C:
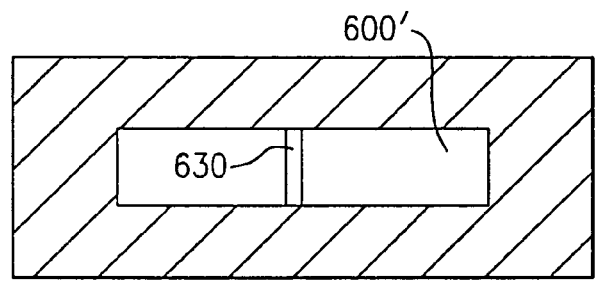
FIG. 19C shows a plan view of a channel that is populated with a weir structure.
Figure 19D:
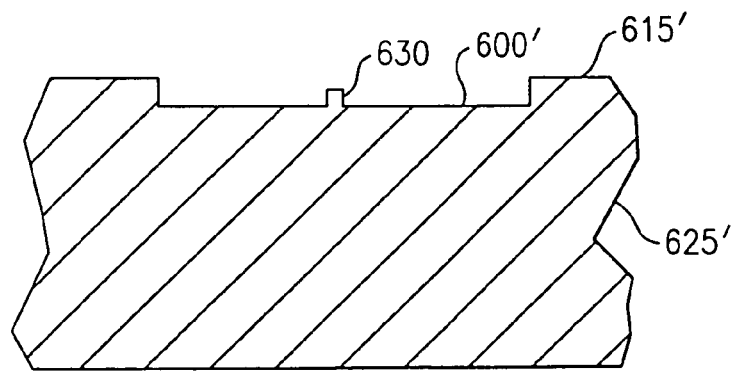
FIG. 19D shows a cross-sectional view of the channel of FIG. 19C after etching is completed.
Figure 19E:
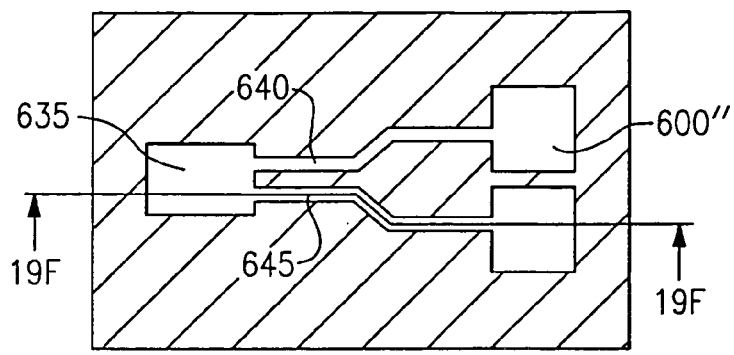
FIG. 19E depicts a plan view of a multi-channel device.
Figure 19F:
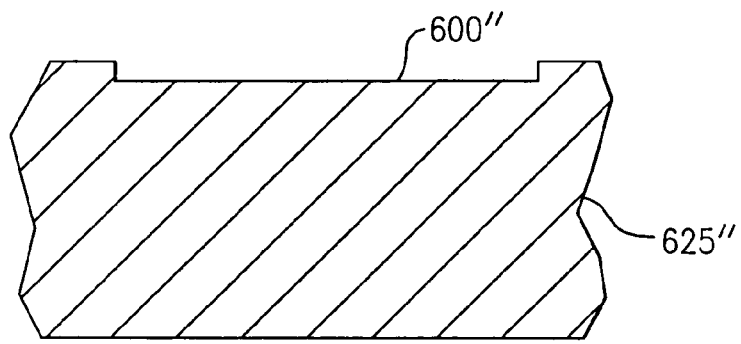
FIG. 19F shows a cross-sectional view of the multi-channel device shown in FIG. 19E taken through line A–A'.

Both of the principal aspects of the present invention—ultra-shallow channels and stepped channels—may be used in alternative embodiments wherein the fluid channels so fabricated may be populated by structures of various kinds, including, but not limited to, posts, weirs, and sub-channel. FIGS. 19A and 19B show plan and cross-sectional views, respectively, of a channel populated with circular posts. FIGS. 19C and 19D show plan and cross-sectional views, respectively, of a channel containing a weir. FIGS. 19E and 19F show plan and cross-sectional views, respectively, of a channel that splits, going from left to right, into two sub-channels. The purpose of these additional structures would be to effect chromatographic separation, to promote mixing, and to partition the fluid into separate channels, for example.

Figure 20:
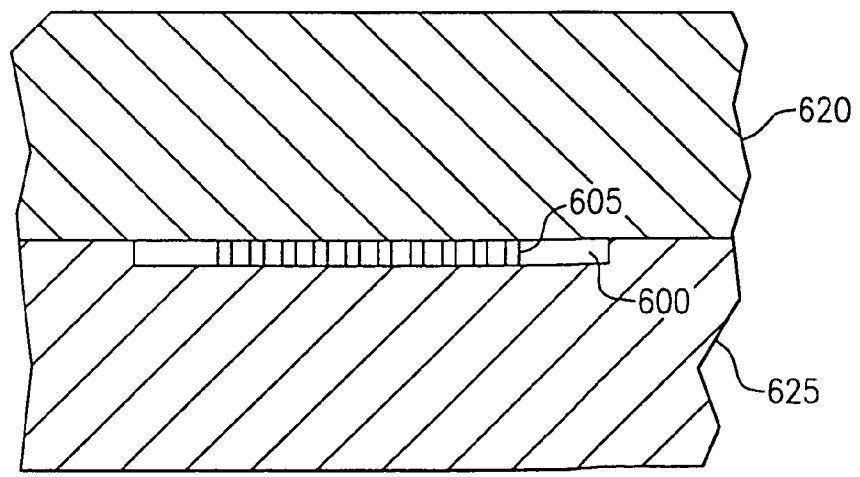
FIG. 20 shows a containing surface attached to the channel substrate of FIGS. 19A and 19C.

The creation of desired structures in the fluid channels can be accomplished simultaneously with formation of the channels themselves. The lithographic mask—or, in the case of stepped channels, the several masks—would define patterns corresponding to the desired structure in addition to defining the extents of the channels themselves. FIG. 19A depicts a plan view of a channel 600 that is populated with posts 605. FIG. 19B shows a cross-sectional view of the resulting channel 600 after etching is completed. In one embodiment, the top surface 610 of the intra-channel structures is co-planar with the major surface 615 surrounding the channel 600. This ensures that there will not be unintended fluid flow paths after a lid substrate 620 is attached to the channel substrate 625 (FIG. 20). FIG. 19C depicts a plan view of a channel 600' that is populated with a weir structure 630. FIG.

19D shows a cross-sectional view of the resulting channel 600' after etching is completed. In this case the weir structure 630 has been etched into the silicon substrate 625' such that the top is intentionally not coplanar with the surrounding field region 615'.

Referring to FIG. 19E, a plan view is shown of a multi-channel device 10. Device 10 includes channel 600" comprising a first segment 635 that is split, in moving from left to right, into two sub-channels 640 and 645. FIG. 19F shows a cross-sectional view of the multi-segment channel 600" taken through section A–A' as etched into the silicon substrate 625".

Referring to FIG. 20, a cover substrate is shown attached to the channel substrate of FIGS. 19A and 19C. The cover substrate hermetically seals the channel substrate to prevent fluids from leaking. As mentioned above, the cover may be bonded by anodic bonding, fusion bonding, frit bonding, and adhesion bonding.

In the case of stepped channels, intra-channel features can be created, the tops of which are, by design, not co-planar with the surrounding field region. FIGS. 21A–21F show a progression of plan and cross-sectional views of a two-level channel containing a structure 725 that extends only from the bottom of the shallower segment 730 to the bottom of the deeper segment 745. This type of structure may be desired so as to constrict fluid flow as shown in FIG. 19D after a containing substrate 750 is attached to the channel substrate 700. In the case of multiply-stepped channels, structures may be created in any or all of the segments.

Figure 21A:
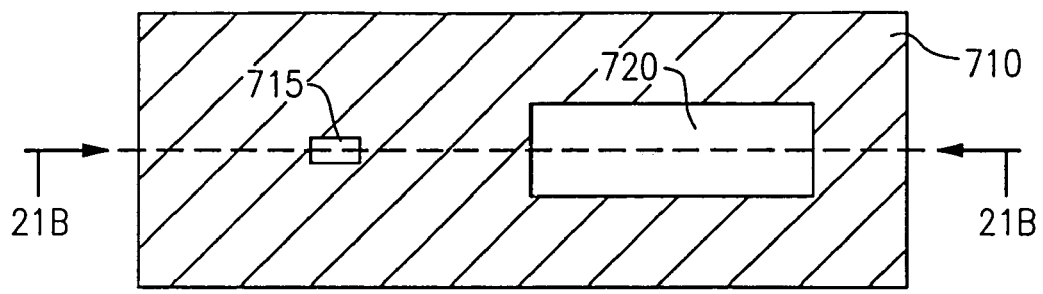
FIG. 21A shows a plan view of a lithographically defined pattern with two open areas surrounded by remaining photoresist.
Figure 21B:
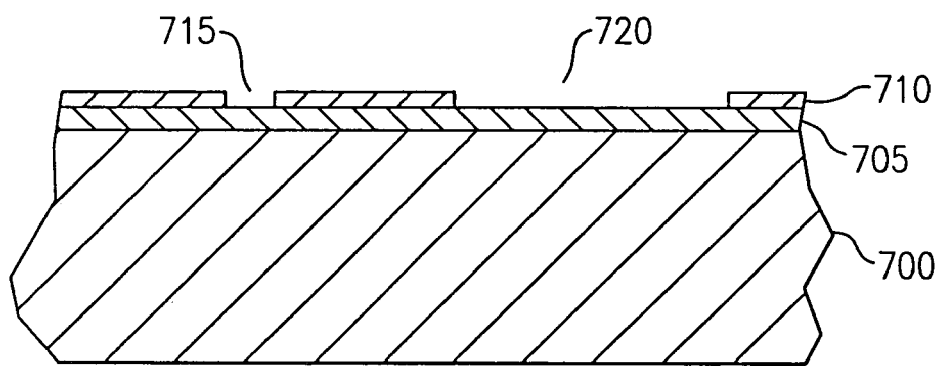
FIG. 21B shows a cross-sectional view taken through section A–A' of the silicon substrate depicted in FIG. 21A.
Figure 21C:
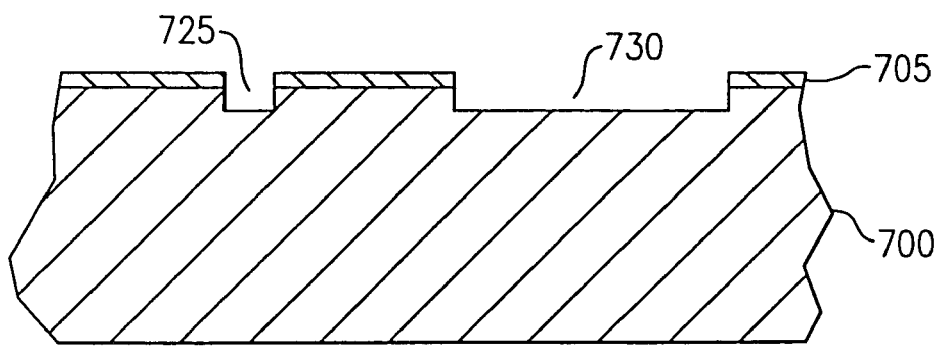
FIG. 21C shows the result of etching through the open areas of FIG. 21A through the underlying oxide layer and into the silicon substrate, followed by removal of any remaining photoresist.
Figure 21D:
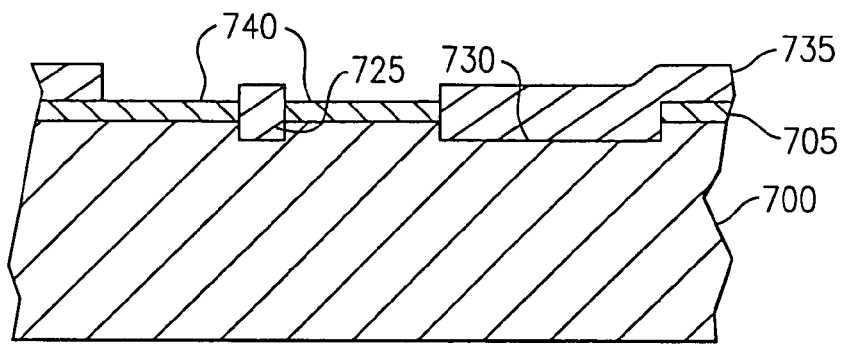
FIG. 21D shows the result of coating a second layer of photoresist followed by lithographic patterning to create additional open areas.
Figure 21E:
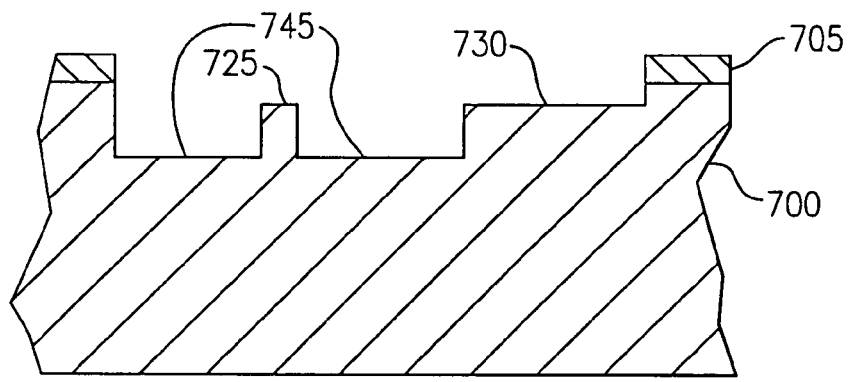
FIG. 21E shows the result of etching through the additional open areas through the underlying oxide layer and into the silicon substrate, followed by removal of any remaining photoresist.
Figure 21F:
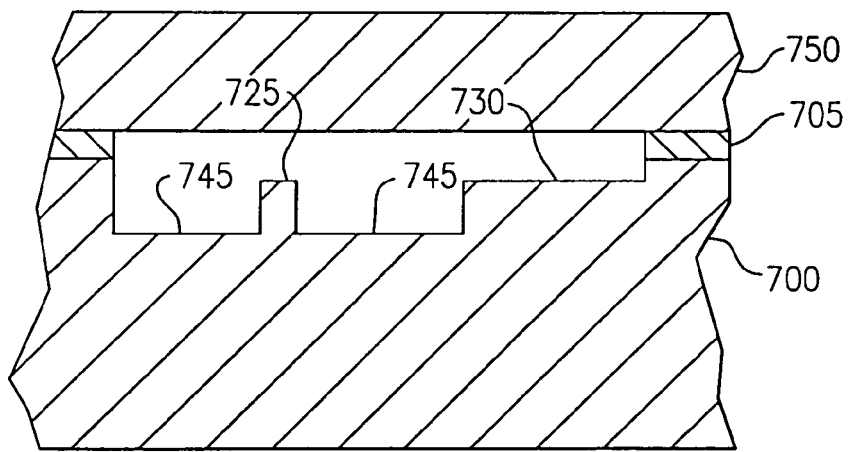
FIG. 21F shows a lid substrate bonded to the channel substrate in order to seal the channel segments.

FIG. 21A shows a plan view of a lithographically defined pattern comprising two open areas 715 and 720, surrounded by remaining photoresist 710. FIG. 21B shows a cross-sectional view taken through section A–A' shown in FIG. 21A. As depicted, silicon oxide layer 705 is disposed on silicon substrate 700. Silicon oxide layer 705 may have been grown or deposited on substrate 700. A photoresist layer 710 is also disposed on silicon oxide layer 705. Open areas 715 and 720 have been lithographically defined. FIG. 21C shows the result of etching through open areas 715 and 720 through the underlying oxide layer 705 and into the silicon substrate 700, followed by removal of any remaining photoresist. In this example, resulting pattern 730 constitutes a first channel segment and pattern 725 corresponds to a structure that will ultimately be located within a second channel segment. Ultra-shallow etch depths may be attained through the method taught in the first aspect of the present invention. FIG. 21D shows the result of coating a second layer of photoresist 735, followed by lithographic patterning to create open areas 740. Note that areas 725 and 730, as defined by the lithographic patterning and etching processes shown in FIGS. 21B and 21C, are protected by photoresist layer 735 in FIG. 21D. FIG. 21E shows the result of etching through open areas 740 through the underlying oxide layer 705 and into the silicon substrate 700, followed by removal of any remaining photoresist. In this example, resulting pattern 745 constitutes a second channel segment, surrounding an intra-channel structure 725. Finally, FIG. 21F shows a lid substrate 750 bonded to the channel substrate 700 in order to seal the channel substrate 700.

Figure 22:
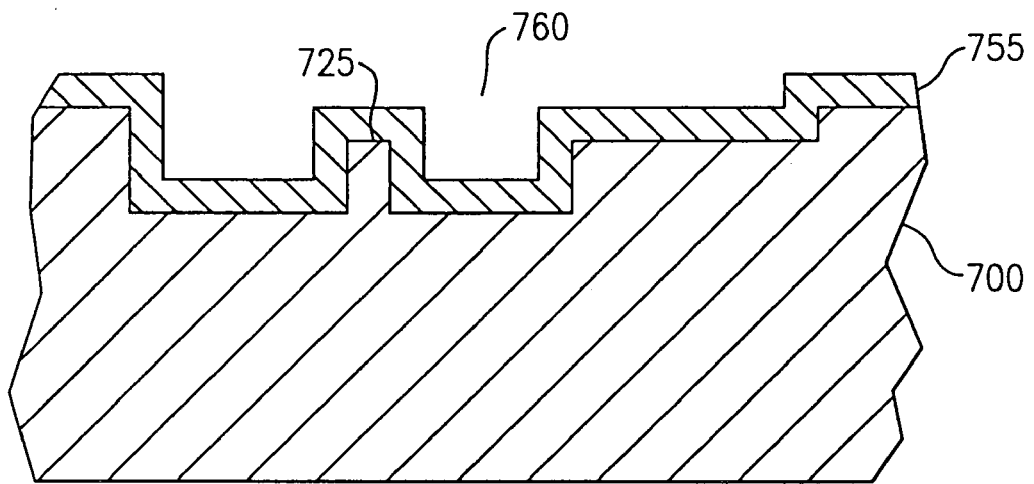
FIG. 22 shows a cross-sectional view of a stepped channel containing a structure in one segment that has been passivated by growth or deposition of a passivating film.

As in the instances of channels and/or structures of ultra-shallow depth(s), the surfaces of structures formed in the channels may be passivated by thermal growth of silicon oxide or by the deposition of a passivating film like silicon oxide or silicon nitride. These processes will preserve the depth of the channel relative to the surrounding field region. FIG. 22 shows a cross-sectional view of a stepped channel 760 containing a structure 725 in one segment that has been passivated by growth or deposition of a passivating film 755 such as thermal oxide, LPCVD silicon oxide, LPCVD silicon nitride, PECVD silicon oxide, or PECVD silicon nitride.

The ultra-shallow fluidic channels or structures so formed—whether passivated or unpassivated—are compatible with a variety of bonding methods for purposes of providing a necessary containing surface for the channels.

Microfluidic Channel System

Figure 23:
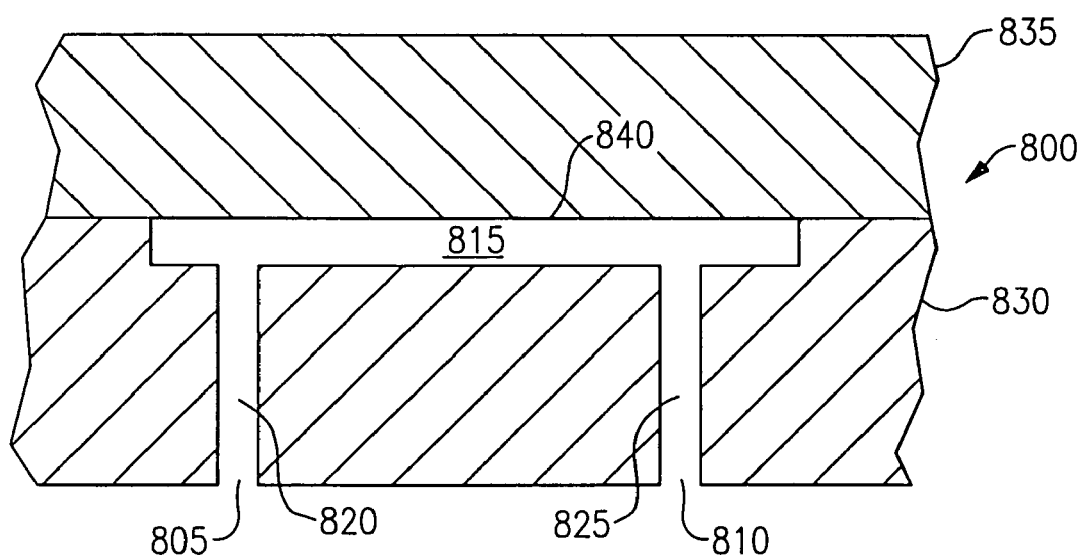
FIG. 23 shows an embodiment of a fluidic channel system, with a ultra-shallow and/or stepped fluidic channel substrate to which a second fluid-confining substrate is attached.

We also disclose a fluidic channel system, comprising a ultra-shallow and/or stepped fluidic channel substrate to which a second fluid-confining substrate is attached. The purpose of the second substrate is to provide the otherwise missing surface to form an enclosed channel. FIG. 23 shows one embodiment of such a system 800. Ingress 805 and egress 810 to/from a fluidic channel 815 in this case, for example, are provided by through-substrate channels 820 and 825 in the channel substrate 830. Fluidic channel 815 is a ultra-shallow combination and/or a stepped fluidic channel. Lid substrate 835 is shown bonded to the channel substrate 830, providing the top surface 840 for the channel 815. Many alternative embodiments, shown in FIGS. 24A–24D, for example, are possible, including all permutations of ingress/egress (1) through the channel substrate, (2) through the lid substrate, and (3) off-chip at the edge of the channel substrate.

Figure 24A:
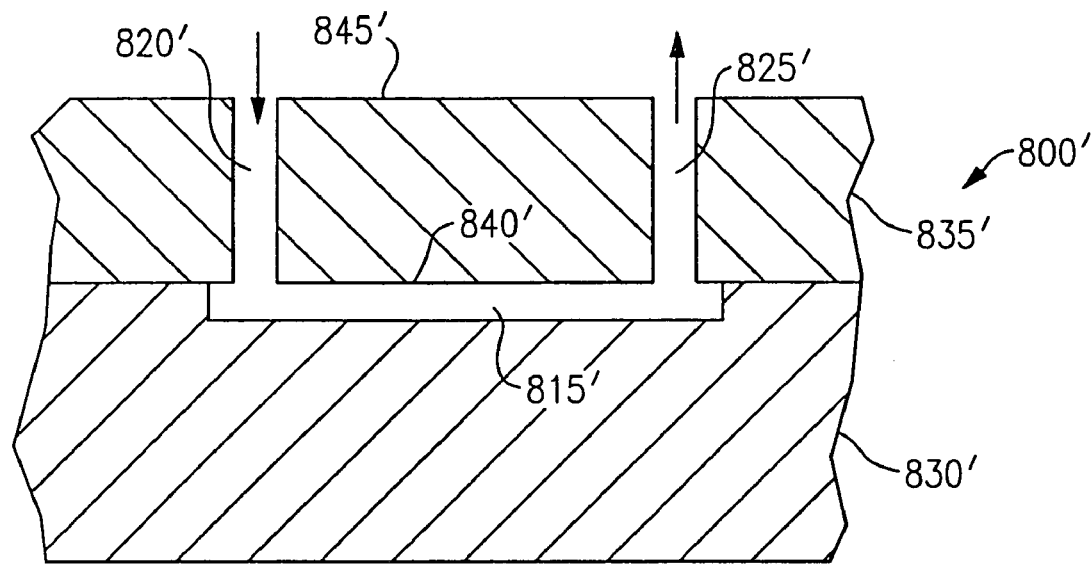
FIG. 24A shows a fluidic channel system produced according to an embodiment of the invention with a channel substrate and a lid substrate, with a ultra-shallow channel etched into the channel substrate.

FIG. 24A shows a fluidic channel system 800' comprising a channel substrate 830' and a lid substrate 835', with a ultra-shallow channel 815' etched into the channel substrate 830'. Ingress and egress channels 820' and 825', respectively, are provided in the lid substrate 835' so as to effect fluidic communication between the top 845' and bottom 840' surfaces of the lid substrate 835' and to thereby provide a means of delivering fluid to the ultra-shallow channel 815' and a means of fluid removal from the channel 815'.

Figure 24B:
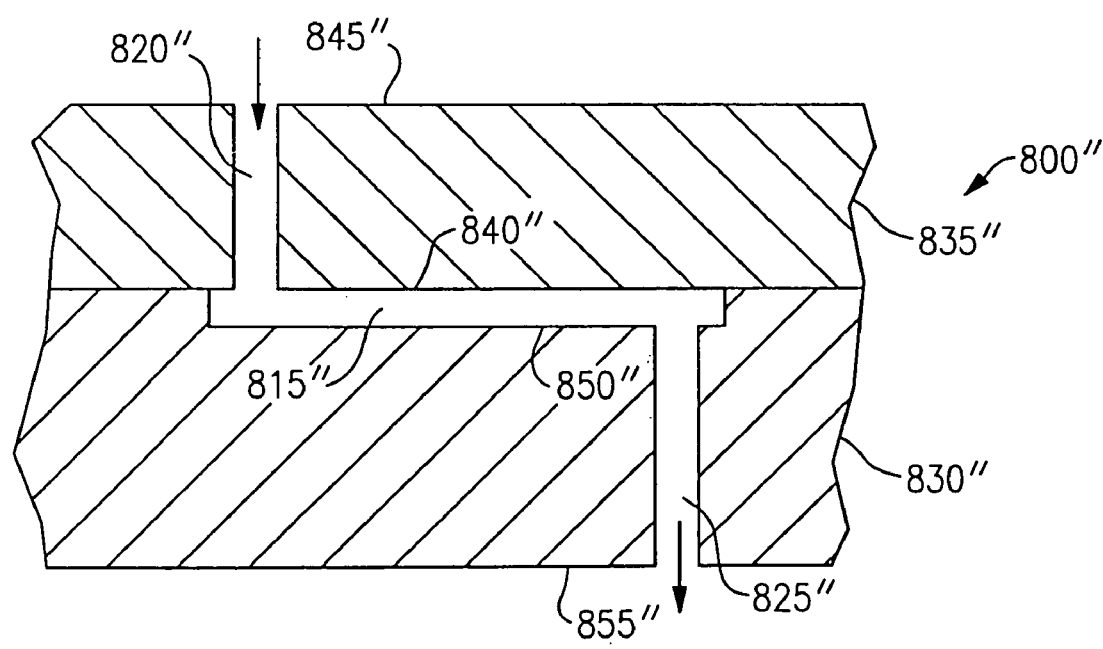
FIG. 24B shows a fluidic channel system produced according to an embodiment of the invention with a channel substrate and a lid substrate, with a ultra-shallow channel etched into the channel substrate.

FIG. 24B shows a fluidic channel system 800" comprising a channel substrate 830" and a lid substrate 835", with a ultra-shallow channel 815" etched into the channel substrate 830". An ingress channel 820" is provided in the lid substrate 835" so as to effect fluidic communication between the top 845" and bottom 840" surfaces of the lid substrate 835" and to provide a means of delivering fluid to the ultra-shallow channel 815". An egress channel 825" is provided in the channel substrate 830" so as to effect fluidic communication between the top 850" and bottom 855" surfaces of the channel substrate 830" and to provide a means of removing fluid from the channel 815".

Figure 24C:
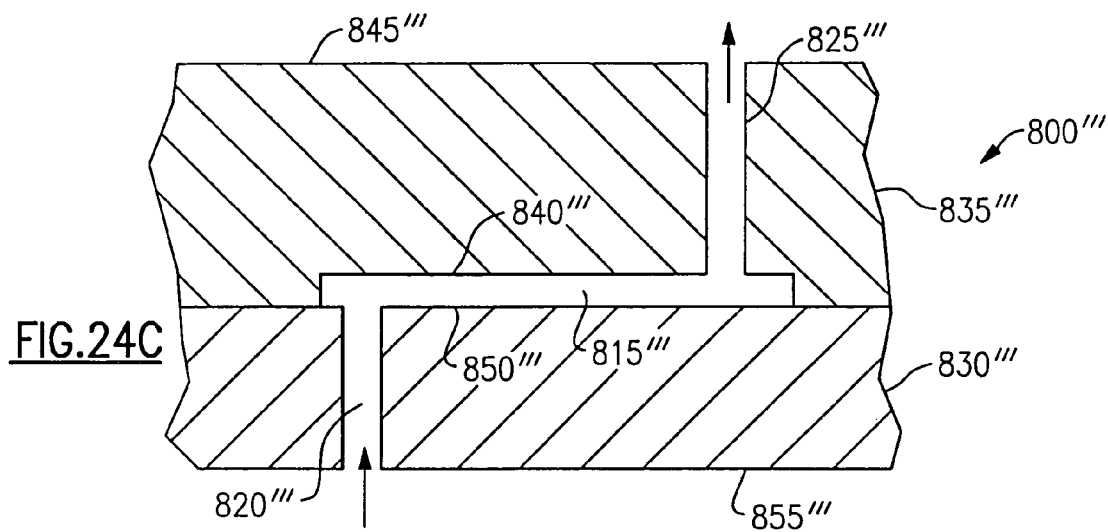
FIG. 24C shows a fluidic channel system produced according to an embodiment of the invention which is similar to the system of FIG. 24B, differing only in the assigned roles of ingress and egress channels.

FIG. 24C shows a fluidic channel system 800''' similar to that of FIG. 24B, differing only in the assigned roles of ingress and egress channels, 820''' and 825''', respectively, but otherwise identical in form and method of fabrication.

Figure 24D:
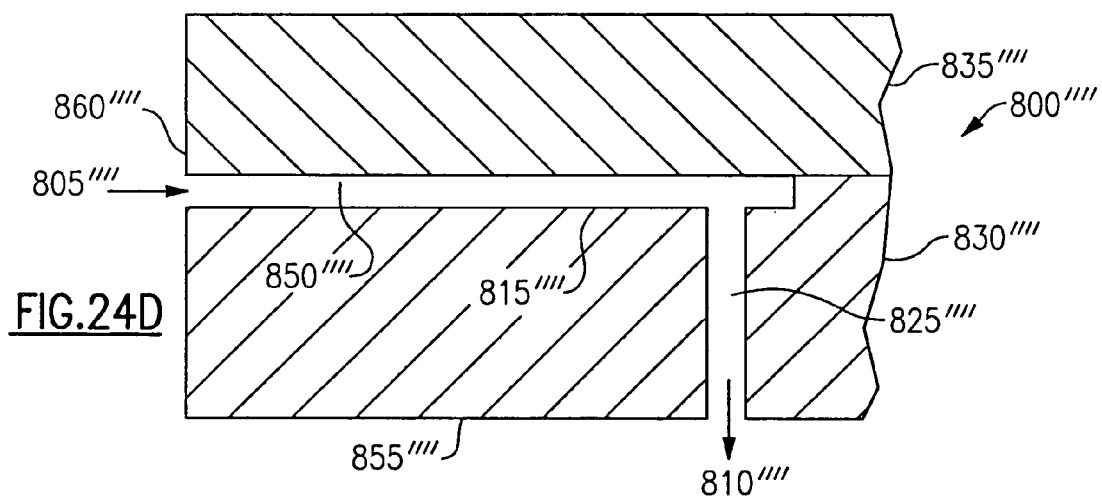
FIG. 24D shows a fluidic channel system produced according to an embodiment of the invention with a channel substrate and a lid substrate, with a ultra-shallow channel etched into the channel substrate and extending to the edge of the channel substrate in the finished/diced form of the system.

FIG. 24D shows a fluidic channel system 800'''' comprising a channel substrate 830'''' and a lid substrate 835'''', with a ultra-shallow channel 815'''' etched into the channel substrate 830'''' and extending to the edge 860'''' of the channel substrate 830'''' in the finished/diced form of the system 800''''. In this example, fluid ingress 805'''' is by means of the channel opening at the system's edge 860'''' and fluid egress 810'''' is by means of a channel 825'''' extending from the top 850'''' to the bottom 855'''' surface of the channel substrate 830'''' such that the surfaces 850'''' and 855'''' are in fluidic communication.

The principal requirements of the attachment method are (1) preservation of designed volume (i.e., minimization, preferably elimination, of offset between channel substrate and lid substrate); (2) hermetic containment of fluid (i.e., no lateral leakage out of the channel); (3) ability to withstand up to several hundred psi fluid pressure without delamination/detachment; (4) prevention of the intrusion of any bonding media into the channels or the channels' ingress and egress openings.

Anodic bonding is the preferred embodiment of the system. Other attachment methods may be used in alternative embodiments, including, but not limited to, fusion bonding methodologies, frit bonding, and adhesion bonding, generally with less complete satisfaction of the aforementioned system requirements.

Figure 25:
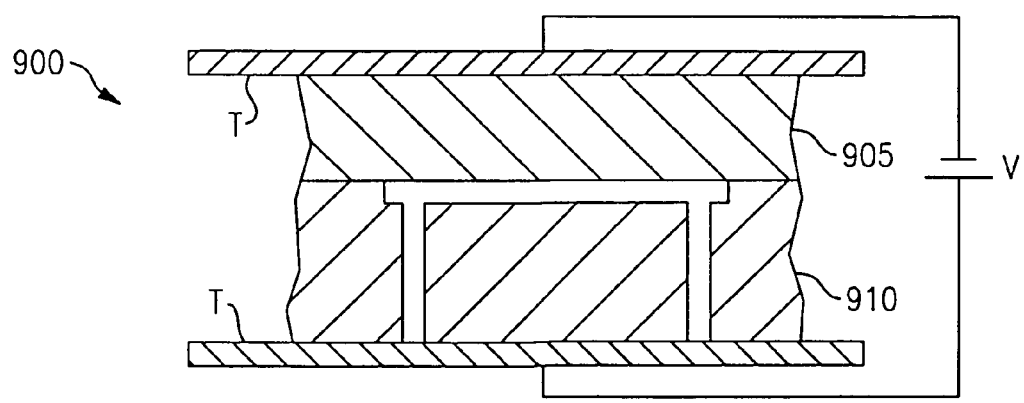
FIG. 25 shows two bonding surfaces brought into intimate contact, with pattern-pattern alignment as necessary, along with the application of heat and electrical potential, to complete anodic bonding.

The anodic bonding process is practiced in the preferred embodiment as a means of attaching the lid substrate 905 to the channel substrate 910 to form a fluid channel system 900. A critical requirement for successful anodic bonding is that both substrates must be essentially particle- and contamination-free on the bonding surface. Standard cleaning methodologies will generally suffice to ensure a proper degree of cleanliness. As shown in FIG. 25, the two bonding surfaces are brought into intimate contact, with pattern-pattern alignment as necessary. FIG. 25 also shows the application of heat and electrical potential, typically 400° C. and 700 V, respectively. Bonding time at these conditions is of the order of five minutes. After cool down, the substrates are firmly attached.

Fluidic channel systems are thus formed in which fluid flow is confined to defined channels. Through the formation of ultra-shallow channels, extremely small volumes of fluid may be directed from source to destination. The system so described is fully compatible with channels of a single depth, stepped channels, and with unstepped or stepped channels containing intra-channel structures.

According to the present invention, a microfluidic channel system which includes at least one MEMS device is contemplated. The MEMS device might include a first substrate that has at least one microstructure formed in the first substrate. The at least one microstructure includes at least one channel structure of submicron channel depth, such as in the range of between about 20 nm and about 1,000 nm.

As described herein, the microstructure typically includes a cover substrate bonded (by, for example, anodic, fusion, frit, or adhesion bonding) to the first substrate, the cover substrate being configured to enclose the at least one channel structure and hermetically seal the MEMS device. The MEMS device also might include a fluid ingress port disposed in either the first substrate or the cover substrate (or both) in fluidic communication with the at least one channel structure, and a fluid egress port disposed in either the first substrate or the cover substrate (or both) in fluidic communication with the fluid ingress port via the at least one channel structure.

Microfluidic channel systems according to the invention can have many varieties, depending on, for example, the functionality one skilled in the art wishes to impart to the systems. Thus, for example, the MEMS device could include multiple substrates, multiple channel structures, or a single channel structure with one or more sub-channels. Further, and in accordance with the present invention, preferentially shaped structures, such as posts or weirs, could be disposed in any given channel. Each MEMS device used in the microfluidic channel system could also include other microstructures, such as fluid reservoirs, or fluid reservoirs connected by channels.

Microfluidic channel systems, and other systems according to the present invention, are well-suited for use in the context of systems for carrying out industrial processes, such as electrospray ionization (ESI) and liquid chromatography (LC), and the like.

A system for performing such processes might include, by way of example, one or more MEMS devices (as described herein), one or more application specific integrated circuits (ASICS), and a computer. The ASIC(s) could be configured, for example, to monitor and/or control the MEMS devices in accordance with instructions stored on and/or executed by the computer.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed is:

1. A method for etching an ultra-shallow channel, comprising the steps of: providing a substrate of a first material; forming a layer of a second material on at least part of said first material; selectively removing a portion of said second material such that said second material is completely removed in at least one area to expose at least one area of said first material and is at least partially persistent in areas adjacent to said at least one exposed area of said first material so as to provide direct etchant communication with said first material within said at least one exposed area and to prevent etchant communication with said first material in areas where said second material has not been completely removed, and such that said act of removing said portion of said second material does not significantly remove any of said first material; providing an etch process that is selective for said second material and selective to said first material, wherein said etch process preferentially etches said second material at a rate that is significantly greater than that at which said etch process would etch said first material; and applying said etch process to etch said first material to a desired depth of said ultra-shallow channel.

2. A method according to claim 1, wherein said desired depth is in a range from 10 nm to 1000 nm with a precision of approximately 5 nm.

3. A method according to claim 1, wherein said first material is silicon and said second material is silicon oxide.

4. A method according to claim 1, wherein said first material is either silicon oxide, quartz, glass, or silica, and said second material is polycrystalline silicon.

5. A method according to claim 1, wherein said etch process is a reactive ion etch process.

6. A method according to claim 1, further comprising the steps of: depositing a third material in said ultra-shallow channel thereby filling said channel; and smoothing said third material until the exposed side of said third material is coplanar with an exposed side of one of said first and second materials.

7. A method according to claim 1, further comprising the step of passivating all exposed surfaces by thermally growing silicon oxide or depositing a passivating film on all exposed surfaces.

8. A method for etching an ultra-shallow channel, comprising the steps of: providing a substrate of a first material; forming a masking layer of a second material on at least part of said first material; coating said masking layer with a photoresist layer; defining a pattern in said photoresist layer; transferring said pattern into said masking layer using a dry etching process selective for said second material at a first etch rate until said first material is exposed; and etching said exposed first material using said dry etching process at a rate less than said first etch rate until a desired depth of said ultra-shallow channel is achieved in said first material.

9. A method according to claim 8, wherein said first material is silicon and said second material is silicon oxide.

10. A method according to claim 8, wherein said first material is silicon oxide, quartz, glass, or silica and said second material is polycrystalline silicon.

11. A method according to claim 8, wherein said desired depth is in a range from 10 nm to 1000 nm.

12. A method according to claim 8, wherein said dry etching process is reactive ion etching.

13. A method according to claim 8, further comprising the steps of: depositing a third material in said ultra-shallow channel thereby filling said channel; and smoothing said third material until a the exposed side of said third material is coplanar with an exposed side of one of said first and second materials.

14. A method according to claim 8, further comprising the step of passivating all exposed surfaces by thermally growing silicon oxide or depositing a passivating film on all exposed surfaces.

15. A method for etching an ultra-shallow channel, comprising the steps of: providing a substrate of a first material; forming a masking layer of a known depth of a second material on at least part of said first material; determining a first etch rate of a dry etching process in said first material where said dry etching process is selective for said second material; determining a second etch rate of said dry etching process in said second material; coating said masking layer with a photoresist layer; defining a pattern in said photoresist layer; transferring said pattern into said masking layer using said dry etching process; and continuing etching said first material using said dry etching process until a desired depth of said ultra-shallow channel is achieved in said first material, where a total time for etching said first and second materials is determined by dividing said desired depth in said first material by said first etch rate to obtain a first time, dividing said known depth of said masking layer by said second etch rate to obtain a second time, and adding said first and second times together to obtain said total time.

16. A method according to claim 15, wherein said first material is silicon and said second material is silicon oxide.

17. A method according to claim 15, wherein said first material is either silicon oxide, quartz, glass, or silica, and said second material is polycrystalline silicon.

18. A method according to claim 15, wherein said desired depth is in a range from 10 nm to 1000 nm with a precision of 5 nm or greater.

19. A method according to claim 15, wherein said dry etching process is reactive ion etching.

20. A method according to claim 15, further comprising the steps of: depositing a third material in said ultra-shallow channel thereby filling said channel; and smoothing said third material until the exposed side of said third material is coplanar with an exposed side of one of said first and second materials.

21. A method according to claim 15, further comprising the step of passivating all exposed surfaces by thermally growing silicon oxide or depositing a passivating film on all exposed surfaces.

22. A method for etching an ultra-shallow channel, comprising the steps of: providing a substrate of a first material; coating said first material with a photoresist layer; defining a pattern in said photoresist layer; transferring said pattern into said first material using a dry etching process selective for a material other than said first material until a desired depth of said ultra-shallow channel is achieved in said first material.

23. A method according to claim 22, wherein said first material is silicon.

24. A method according to claim 22, wherein said desired depth is in a range from 10 nm to 1000 nm, with a precision of 5 nm or greater.

25. A method according to claim 22, wherein said dry etching process is reactive ion etching.

26. A method according to claim 22, further comprising the steps of: depositing a second material in said ultra-shallow channel thereby filling said channel; and smoothing said second material until the exposed side of said second material is coplanar with an exposed side of said first material.

27. A method according to claim 22, further comprising the step of passivating all exposed surfaces by thermally growing silicon oxide or depositing a passivating film on all exposed surfaces.

28. A method for etching an ultra-shallow channel in a workpiece, comprising the steps of: providing a substrate of a first material; forming a layer of a second material on at least part of said first material; coating said layer with a photoresist; defining a pattern in said photoresist; and transferring said pattern into said layer using a dry etching process selective for said first material until a desired depth of said ultra-shallow channel is achieved in said second material.

29. A method according to claim 28, wherein said ultra-shallow channel includes a first reservoir section, first and second subchannels connected to said first reservoir section, and second and third reservoir sections connected to said first and second subchannels, respectively, wherein said first, second, and third reservoir sections and said first and second subchannels are all at said desired depth.

30. A method according to claim 29, further comprising affixing a containing surface to said layer.

31. A method according to claim 28, wherein said first material is silicon and said second material is silicon oxide.

32. A method according to claim 28, wherein said first material is either silicon oxide, quartz, glass, or silica, and said second material is polycrystalline silicon.

33. A method according to claim 28, wherein said desired depth is in a range from 10 nm to 1000 nm, with a precision of 5 nm or greater.

34. A method according to claim 28, wherein said dry etching process is reactive ion etching.

35. A method according to claim 28, further comprising the steps of: depositing a third material in said ultra-shallow channel etched in said layer of said second material that is formed on said substrate, thereby filling said channel; smoothing said third material until the exposed side of said third material is coplanar with an exposed side of one of said first and second materials.

36. A method according to claim 35, wherein said third material is metal.

37. A method according to claim 35, wherein said third material is electrically conductive.

38. A method according to claim 35, wherein said substrate is silicon that is doped with one conductivity and said third material is deposited silicon that is doped with another conductivity.

39. A method according to claim 35, further comprising the step of forming an insulating layer in said ultra-shallow channel over said substrate before said step of depositing.

40. A method according to 28, further comprising the step of passivating all exposed surfaces by thermally growing silicon oxide or depositing a passivating film on all exposed surfaces.

41. A method for creating a structure that is attached to a substrate only at designated anchor points, thus permitting free movement of said structure except at said anchor points, comprising the steps of: providing a workpiece initially consisting of a substrate of a first material; forming a layer of a second material on at least part of said first material; coating said layer with a photoresist; defining a pattern for said anchor points in said photoresist; transferring said pattern into said layer using a dry etching process selective for said first material until a depth of said pattern in said second material extends to substrate; depositing said first material in said pattern, thereby filling said pattern; smoothing said first material until the exposed side of said first material is coplanar with an exposed side of said second material; depositing said first material on said workpiece followed by patterning said first material; and etching, using a wet etch, to remove said second material, thereby leaving said patterned first material and said substrate connected only by non-patterned regions of said workpiece.

42. A method according to claim 41, wherein a depth of said pattern is ultra-shallow.

43. A method according to claim 41, wherein said first material is silicon and said second material is silicon oxide.

44. A method according to claim 41, further comprising the step of passivating all exposed surfaces by thermally growing silicon oxide or depositing a passivating film on all exposed surfaces.

45. A method for etching a channel, comprising the steps of: providing a substrate of a first material; forming a masking layer of a second material on at least part of said first material; coating said masking layer with a first photoresist layer; defining a first pattern for a first segment of said channel in said first photoresist layer; transferring said first pattern into said masking layer using a dry etching process selective for said second material at a first etch rate until said first material is exposed; etching, at a second etch rate, said exposed first material using said dry etching process until a desired depth of said first segment of said channel is achieved in said first material; removing said first photoresist layer from said masking layer; coating said masking layer and said first segment with a second photoresist layer; defining a second pattern for a second segment of said channel in said second photoresist layer; transferring said second pattern into said masking layer using said dry etching process selective for said second material until said first material is exposed; etching said exposed first material using said dry etching process until a desired depth of said second segment of said channel is achieved in said first material, wherein said first and second segments have different depths; and removing said second photoresist layer from said masking layer and said first segment.

46. A method according to claim 45, further comprising the step of passivating all exposed surfaces by thermally growing silicon oxide or depositing a passivating film on all exposed surfaces.

47. A method according to claim 45, wherein at least one of said first and second segments is ultra-shallow.

48. A method according to claim 47, wherein said first segment is a weir structure and said second segment is two channel structures separated by said weir structure.

49. A method according to claim 48, further comprising affixing a containing surface to said masking layer.

50. A method according to claim 45, wherein an ultra-shallow segment is adjacent a segment of shallow depth.

51. A method according to claim 45, wherein an ultra-shallow segment is adjacent a segment of standard depth.

52. A method according to claim 45, wherein depths of two adjacent segments vary by a ratio of $10^4$.

53. A method according to claim 45, further comprising the steps of: determining a number n representing n segments to be formed within said channel; coating said masking layer and said first through (n−1) segments with an nth photoresist layer; defining an nth pattern for said nth segment of said channel in said nth photoresist layer; transferring said nth pattern into said masking layer using said dry etching process selective for said second material until said first material is exposed; etching said exposed first material using said dry etching process until a desired depth of said nth segment of said channel is achieved in said first material, wherein at least two of said first through nth segments have different depths; and removing said nth photoresist layer from said masking layer and said first through (n−1) segments.

54. A method according to claim 53, wherein at least one of said first through nth segments is ultra-shallow.

55. A method according to claim 53, wherein an ultra-shallow segment is adjacent a segment of shallow depth.

56. A method according to claim 53, wherein an ultra-shallow segment is adjacent a segment of standard depth.

57. A method according to claim 53, wherein depths of two adjacent segments vary by a ratio of $10^4$.

58. A method according to claim 53, further comprising the step of passivating all exposed surfaces by thermally growing silicon oxide or depositing a passivating film on all exposed surfaces.

59. A method for etching a channel in a workpiece, comprising the steps of: providing a substrate of a first material as an initial form of said workpiece; forming a masking layer of a second material on at least part of said first material; coating said workpiece with a first photoresist layer; defining a first pattern for a first segment of said channel in said first photoresist layer; transferring said first pattern into said masking layer using a dry etching process selective for said second material until said first material is exposed; removing said first photoresist layer from said workpiece; coating a second photoresist layer on said workpiece; defining a second pattern for a second segment of said channel on said second photoresist layer, wherein said second pattern includes said first pattern as a subset; dry etching, after the step of defining said second pattern, said first pattern into said first material for a first period of time; transferring said second pattern into said masking layer using dry etching; and dry etching simultaneously, using said dry etching process and after the step of transferring said second pattern, said first and second patterns for a second period of time, such that the planar dimensions of said first pattern and said second pattern are reproduced in said substrate.

60. A method according to claim 59, further comprising the step of passivating all exposed surfaces by thermally growing silicon oxide or depositing a passivating film on all exposed surfaces.

61. A method according to claim 59, wherein at least one of said first and second segments is ultra-shallow.

62. A method according to claim 59, wherein an ultra-shallow segment is adjacent a segment of shallow depth.

63. A method according to claim 59, wherein an ultra-shallow segment is adjacent a segment of standard depth.

64. A method according to claim 59, wherein depths of two adjacent segments vary by a ratio of $10^4$.

65. A method for etching a channel in a workpiece, comprising the steps of: providing a substrate of a first material as an initial form of said workpiece; forming a masking layer of a second material on said workpiece; coating a first photoresist layer on said masking layer; defining a first pattern for first and second segments of said channel on said first photoresist layer; transferring said first pattern into said masking layer to a depth of an interface between said first material and said second material using dry etching; removing said first photoresist layer from said workpiece; coating a second photoresist layer on said workpiece; defining a second pattern on said workpiece, wherein said second pattern corresponds to said first segment of said channel; dry etching, after the step of defining said second pattern, said second pattern into said first material for a first period of time; removing said second photoresist layer from said workpiece; dry etching simultaneously, using said dry etching process and after the step of dry etching said second pattern, said first and second segments for a second period of time, such that the planar dimensions of said first segment and said second segment are reproduced in said substrate.

66. A method according to claim 65, further comprising the step of passivating all exposed surfaces of said workpiece by thermally growing silicon oxide or depositing a passivating film on all exposed surfaces.

67. A method according to claim 65, wherein at least one of said first and second segments is ultra-shallow.

68. A method according to claim 65, wherein an ultra-shallow segment is adjacent a segment of shallow depth.

69. A method according to claim 65, wherein an ultra-shallow segment is adjacent a segment of standard depth.

70. A method according to claim 65, wherein depths of two adjacent segments vary by a ratio of $10^4$.

71. A method for making a plurality of posts in an ultra-shallow channel in a workpiece, comprising the steps of: providing a substrate of a first material; forming a layer of a second material on at least part of said first material; coating said layer with a photoresist; defining a pattern for said plurality of posts in said photoresist such that said plurality of posts are masked from etching; and transferring said pattern into said layer using a dry etching process selective for said first material until a desired depth of said ultra-shallow channel is achieved in said second material.

72. A method according to claim 71, wherein said first material is silicon and said second material is silicon oxide.

73. A method according to claim 71, wherein said desired depth is in a range from 10 nm to 1000 nm.

74. A method according to claim 71, wherein said dry etching process is reactive ion etching.

75. A method according to claim 71, further comprising the step of passivating all exposed surfaces by thermally growing silicon oxide or depositing a passivating film on all exposed surfaces.

76. A method according to claim 71, further comprising affixing a containing surface to said second material.

77. A method for etching a channel, comprising the steps of: providing a substrate of a first material; forming a masking layer of a second material on at least part of said first material; coating said masking layer with a first photoresist layer; defining a first pattern for a first segment and a second segment of said channel in said first photoresist layer; transferring said first pattern into said masking layer using a dry etching process selective for said second material at a first etch rate until said first material is exposed; etching, at a second etch rate, said exposed first material using said dry etching process until a desired depth of said first and second segments of said channel is achieved in said first material; removing said first photoresist layer from said masking layer; coating said masking layer and said first and second segments with a second photoresist layer; defining a second pattern for a third segment of said channel in said second photoresist layer; transferring said second pattern into said masking layer using said dry etching process selective for said second material until said first material is exposed; etching said exposed first material using said dry etching process until a desired depth of said third segment of said channel is achieved in said first material, wherein said third segment is a different depth from said desired depth of said first and second segments; and removing said second photoresist layer from said masking layer and said first and second segments.

78. A method according to claim 77, wherein said desired depth is in a range from 10 nm to 1000 nm.

79. A method according to claim 77, wherein said dry etching process is reactive ion etching.

80. A method according to claim 77, further comprising the step of passivating all exposed surfaces by thermally growing silicon oxide or depositing a passivating film on all exposed surfaces.

81. A method according to claim 77, further comprising affixing a containing surface to said second material.

* * * * *